United States Patent
Cai et al.

(10) Patent No.: US 10,872,679 B2
(45) Date of Patent: Dec. 22, 2020

(54) MULTIPLEX ANALYSIS OF MOLECULES IN SINGLE CELLS BY IMAGE CORRELATION

(71) Applicant: California Institute of Technology, Pasadena, CA (US)

(72) Inventors: Long Cai, Pasadena, CA (US); Ahmet F. Coskun, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 806 days.

(21) Appl. No.: 14/802,919

(22) Filed: Jul. 17, 2015

(65) Prior Publication Data

US 2016/0019334 A1 Jan. 21, 2016

Related U.S. Application Data

(60) Provisional application No. 62/025,891, filed on Jul. 17, 2014.

(51) Int. Cl.
*G16B 5/00* (2019.01)
*G16B 35/00* (2019.01)
*G16B 45/00* (2019.01)
*G16C 20/60* (2019.01)

(52) U.S. Cl.
CPC .............. *G16B 5/00* (2019.02); *G16B 35/00* (2019.02); *G16B 45/00* (2019.02); *G16C 20/60* (2019.02)

(58) Field of Classification Search
None
See application file for complete search history.

(56) References Cited

U.S. PATENT DOCUMENTS

2014/0031243 A1 1/2014 Cai

FOREIGN PATENT DOCUMENTS

WO WO 2014/078855 A1 5/2014

OTHER PUBLICATIONS

Chen, K. H. et al., "Spatially Resolved, Highly Multiplexed RNA Profiling in Single Cells," Science AAAS, Mar. 18, 2015.
Hanley. M. et al., "Detection of Low Abundance RNA Molecules in Individual Cells by Flow Cytometry," PLoS One, 8(2): e57002 (2013).
Lee, H. et al., "Colour-barcoded magnetic microparticles for multiplexed bioassays," Nature Materials 9, 745-749 (2010).
Lubeck, E. et al., "Single-Cell Systems Biology by Super-Resolution Imaging and Combinatorial Labeling," Nature Methods, vol. 9(7): 743-748 (2012).
Lubeck, E. et al., "Single-Cell in situ RNA Profiling by Sequential Hybridization," Nature Methods 11(4): 360-361 (2012).
Notification of Transmittal of International Search Report and Written Opinion of the International Searching Authority, PCT/US2015/041030, dated Oct. 16, 2015.
Trcek, T., et al., "Single-mRNA Counting Using Fluorescent in Situ Hybridization in Budding Yeast," Nature Protocols 7, 408-419 (2012).
Communication from European Patent Office dated Feb. 19, 2018 for European Patent Application No. 158213447, 10 pages.
Santiago Constantino, et al. Accuracy and dynamic range of spatial image correlation and cross-correlation spectroscopy, Biophysical Journal, vol. 89, Aug. 2005, pp. 1251-1260.
Communication Pursuant to Article 94(3) EPC dated Apr. 8, 2020 issued by the European Patent Office for European Patent Application No. 15821344.7, 9 pages.

*Primary Examiner* — G Steven Vanni
(74) *Attorney, Agent, or Firm* — Squire Patton Boggs (US) LLP

(57) ABSTRACT

Disclosed herein are methods and systems for analyzing visual data from multiple rounds of hybridization interactions where the same molecular target is detected by probes with different detectable labels. In particular, disclosed herein are methods and systems for analyzing sequential hybridization images for molecular profiling, where the images are obtained using multiplex fluorescence in situ hybridization (FISH).

18 Claims, 27 Drawing Sheets

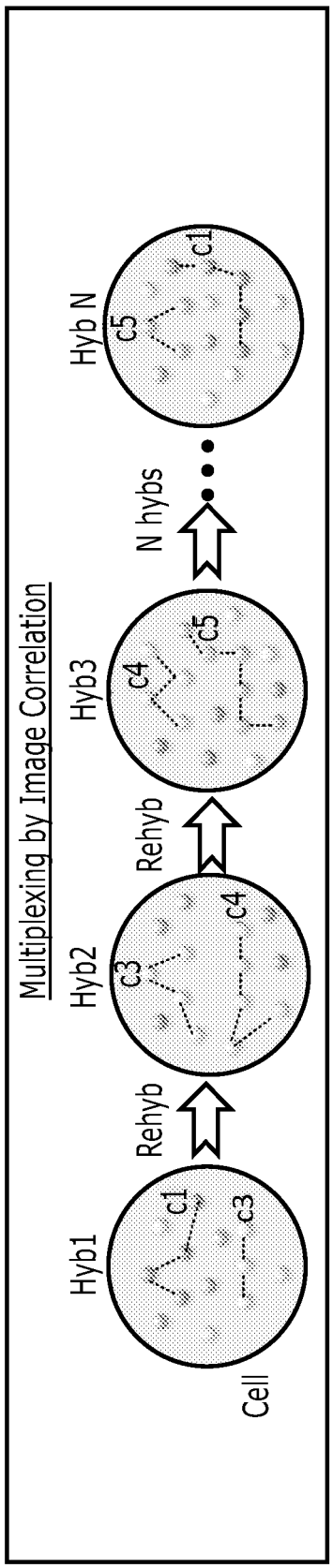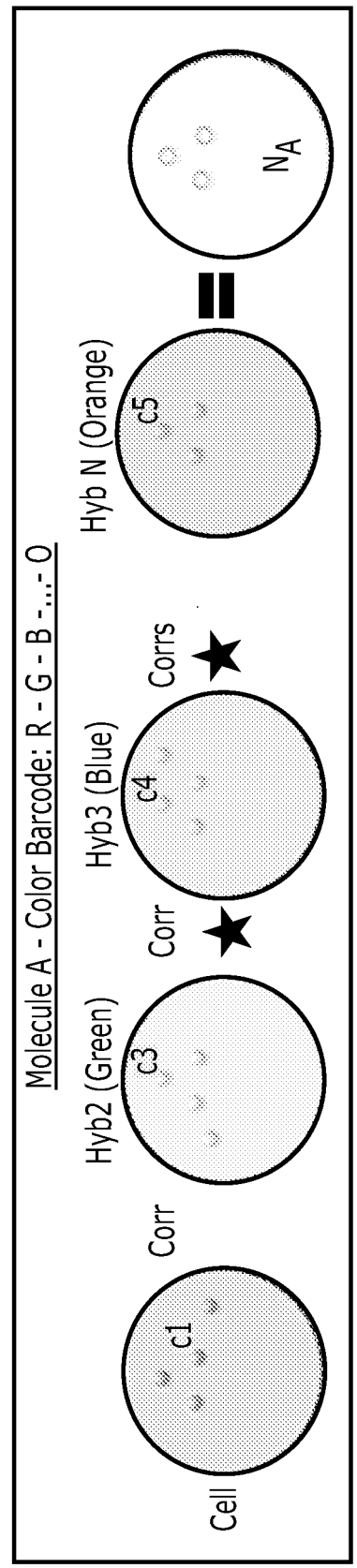
Figure 2A
Figure 2B

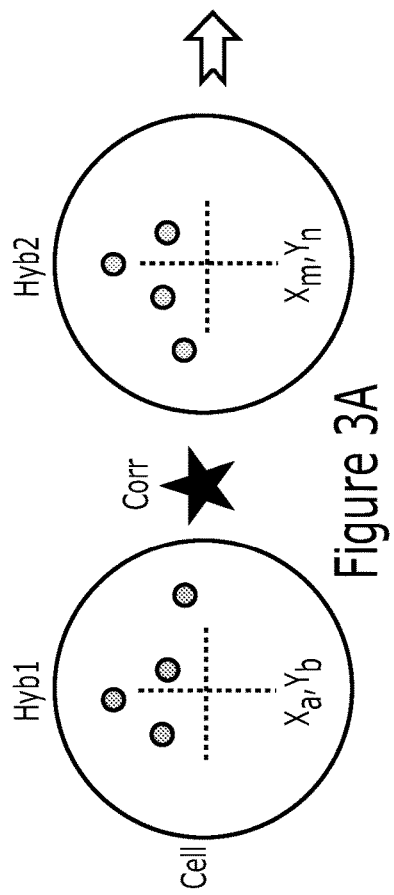
Figure 3A
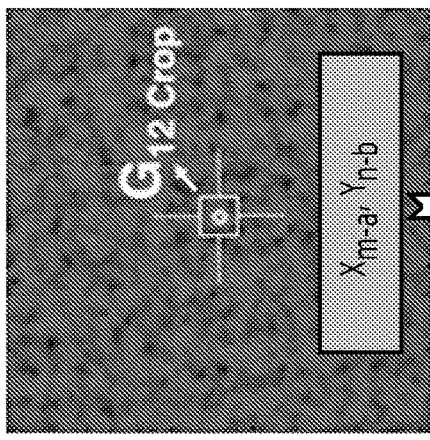
Figure 3B Correlation
Figure 3C Background averaging image filtering
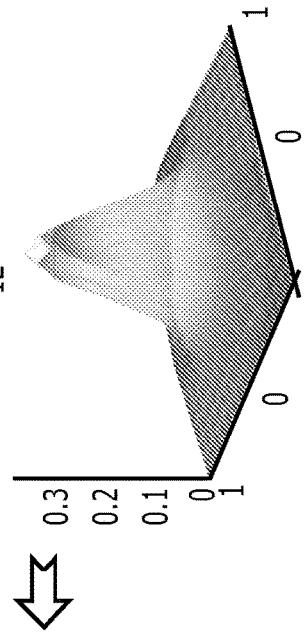
Figure 3D Cross Correlation $G_{12}$ Crop
Figure 3E Molecule Quantitation with Correlations
$$\langle N_N \rangle \approx \frac{1}{G_{NN}(0,0)}$$
$$\langle N_{12} \rangle \approx \frac{G_{12}(0,0)}{G_{11}(0,0)\, G_{22}(0,0)}$$
$$\langle N_{12\ldots N} \rangle \approx \frac{G_{12\ldots N}(0,0)}{G_{11}(0,0)\, G_{22}(0,0)\ldots G_{NN}(0,0)}$$

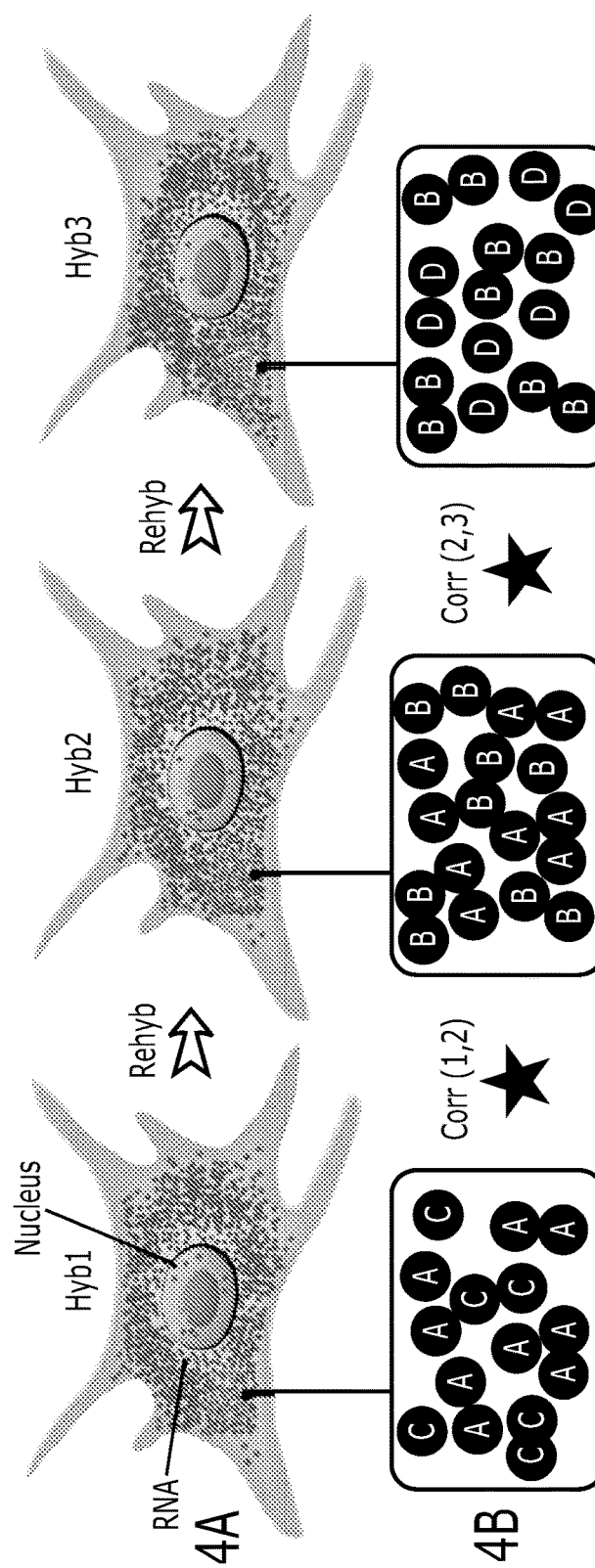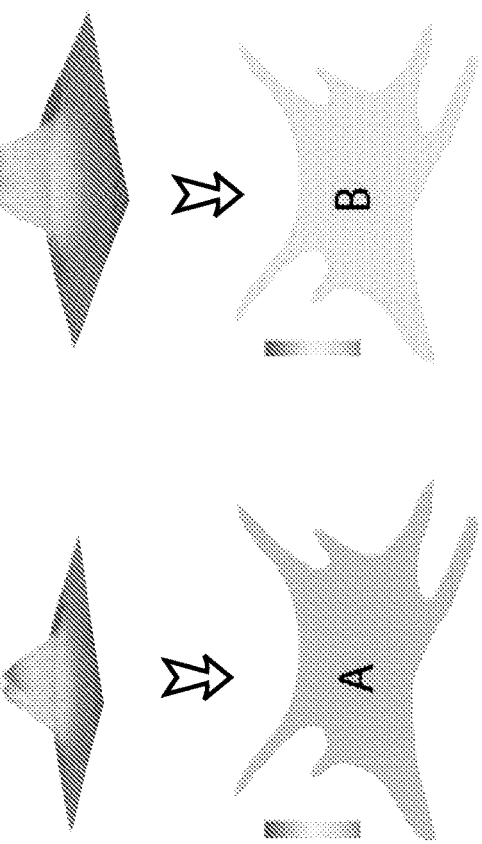
Figure 4A
Figure 4B
Figure 4C
Figure 4D

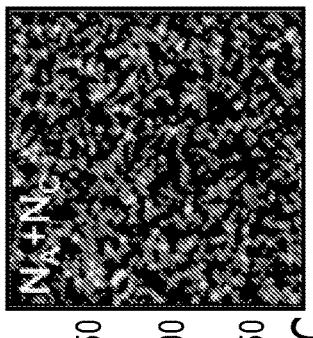
The Emitter Locations
Figure 5A
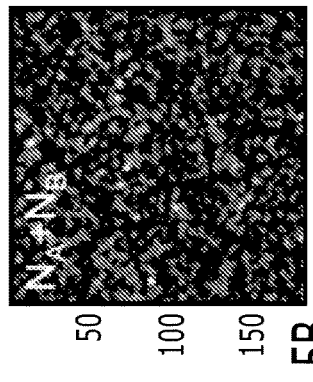
The PSF Blurred Emitters for First Hyb
Figure 5B
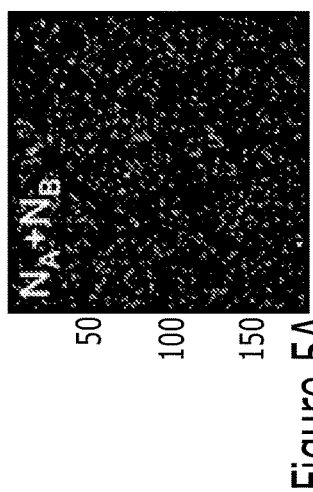
The PSF Blurred Emitters for Second Hyb
Figure 5C
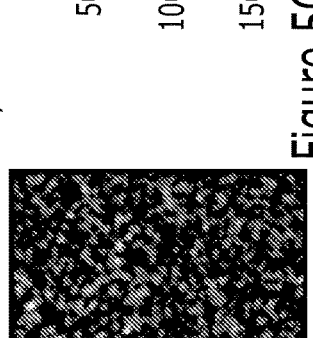
The cross-correlation
Figure 5D
The cross-correlation
Figure 5E
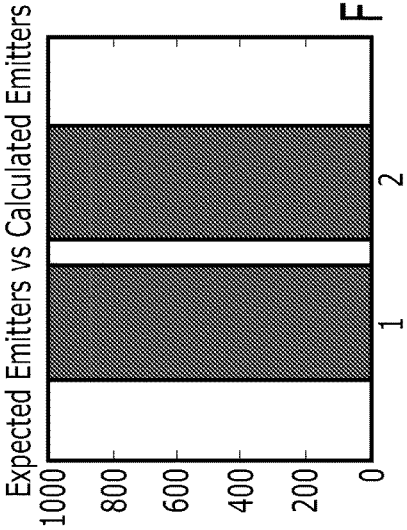
Figure 5F
Figure 5G

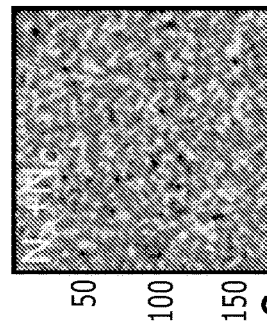
Figure 6A The Emitter Locations
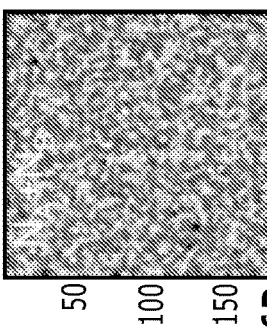
Figure 6B The PSF Blurred Emitters for First Hyb
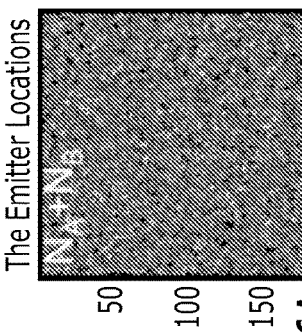
Figure 6C The PSF Blurred Emitters for Second Hyb
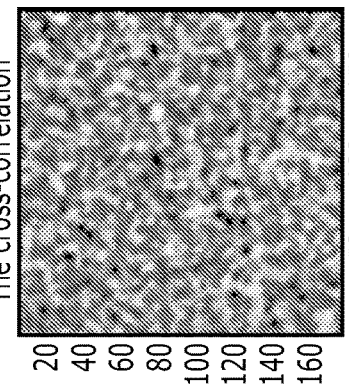
Figure 6D The cross-correlation
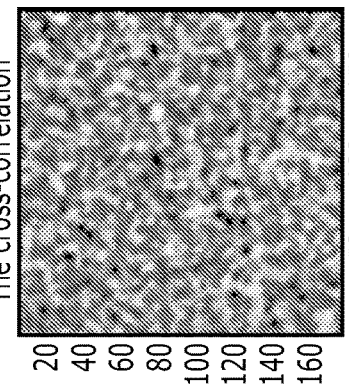
Figure 6E The cross-correlation
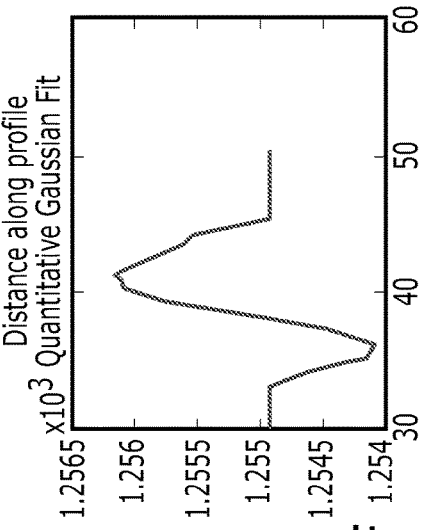
Figure 6F Distance along profile / Quantitative Gaussian Fit
Figure 6G Expected Emitters vs Calculated Emitters

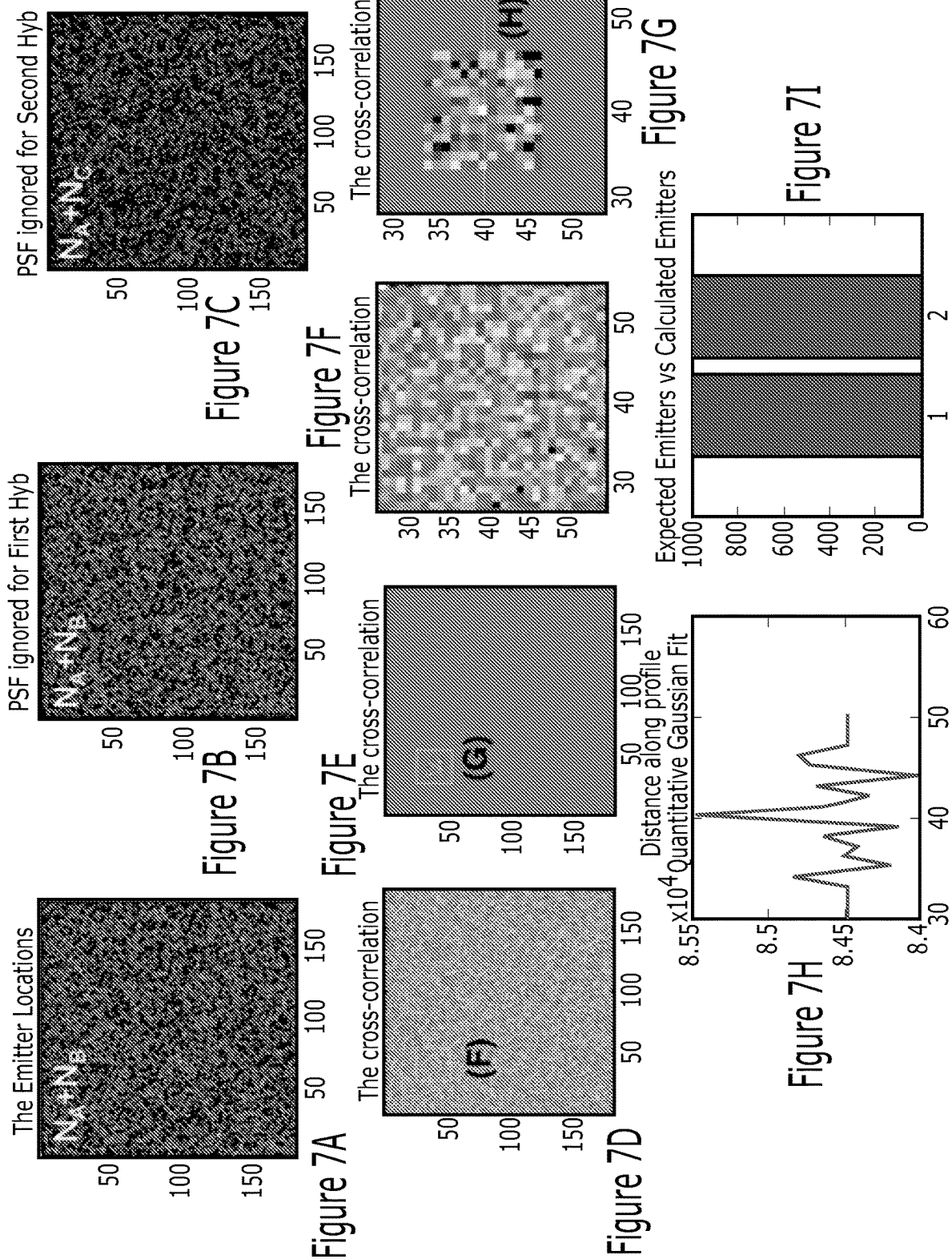

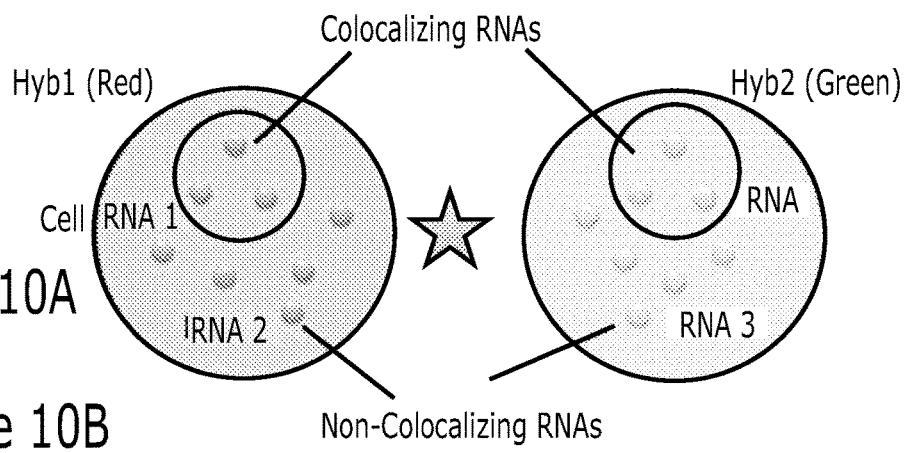
Figure 10A
Figure 10B
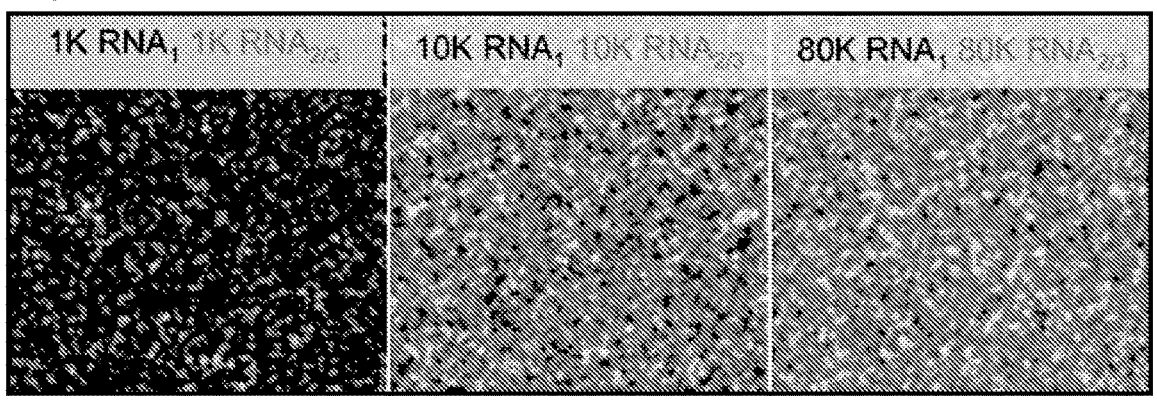
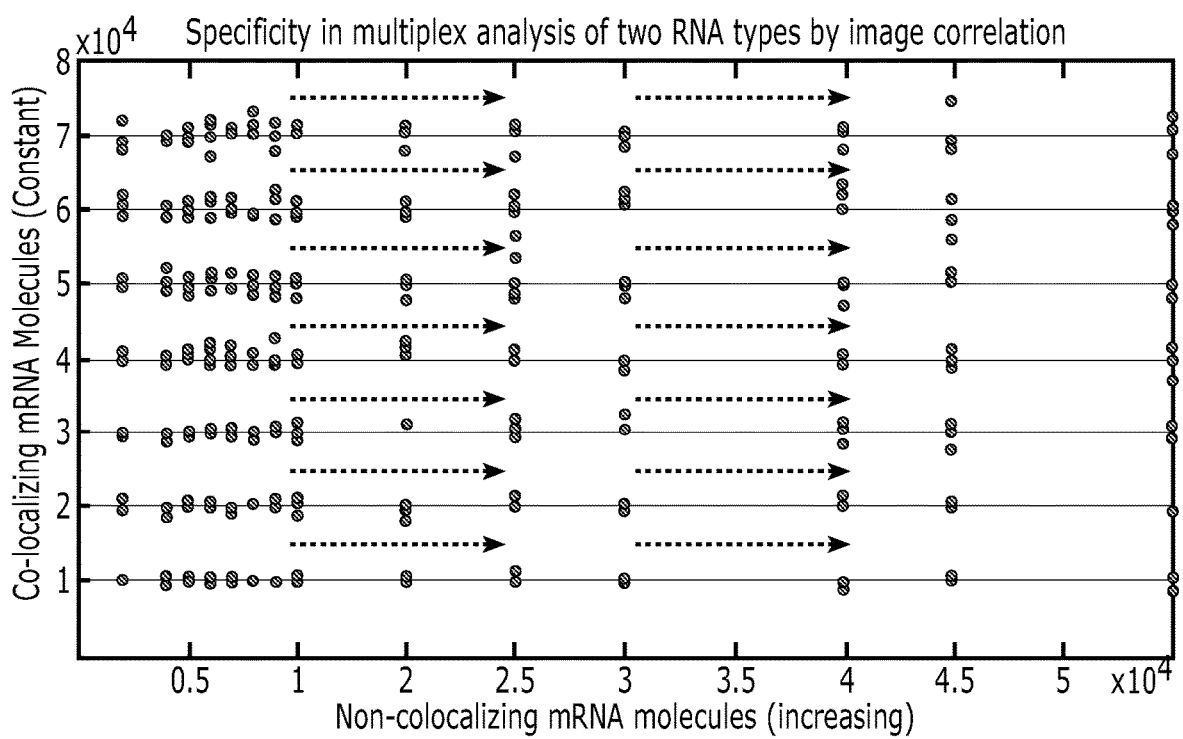
Figure 10C

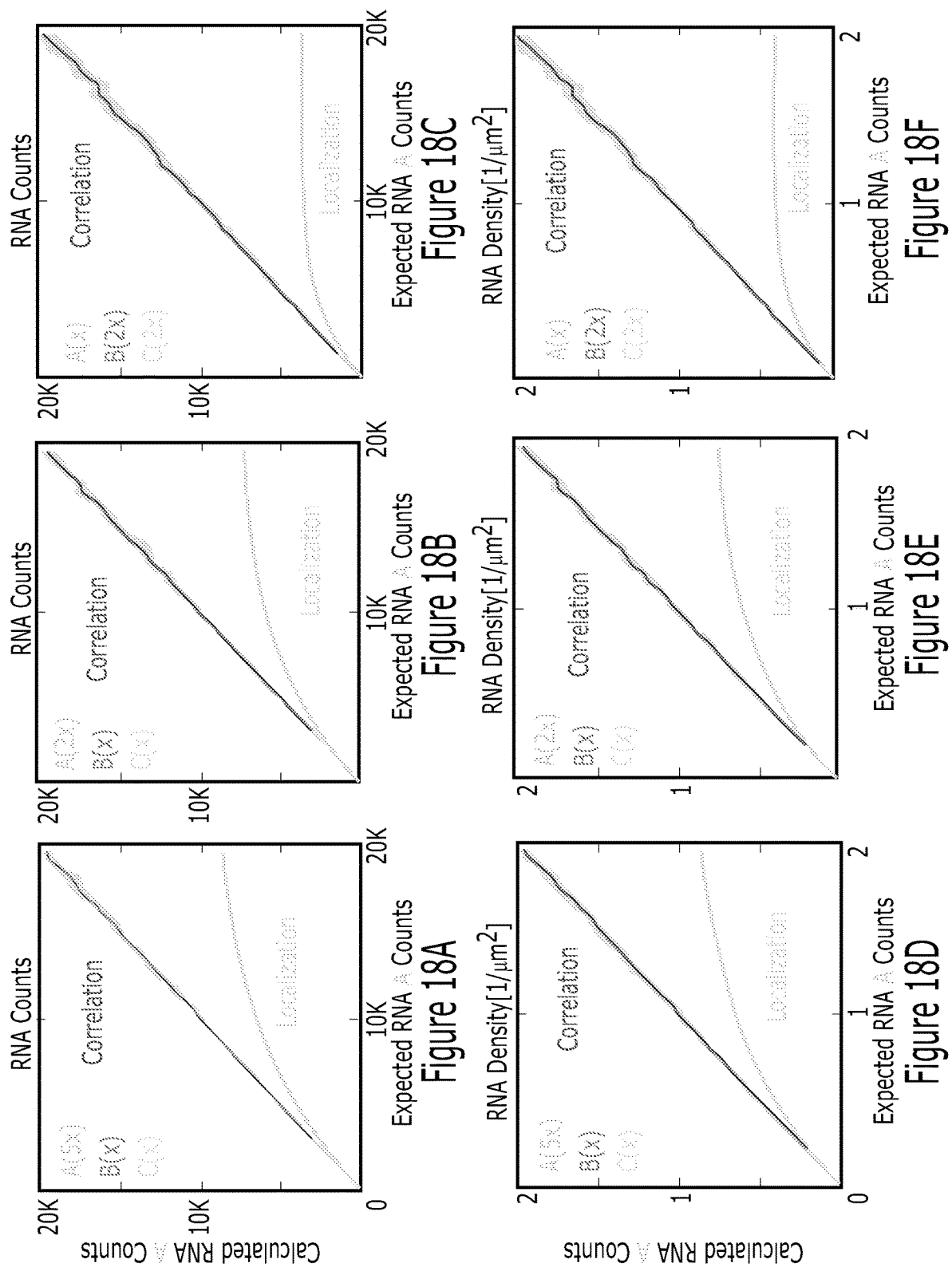

MULTIPLEX ANALYSIS OF MOLECULES IN SINGLE CELLS BY IMAGE CORRELATION

CROSS-REFERENCE TO RELATED APPLICATIONS

This application claims priority to U.S. Provisional Application Ser. No. 62/025,891, filed Jul. 17, 2014, which is hereby incorporated by reference herein in its entirety.

STATEMENT REGARDING FEDERALLY-SPONSORED RESEARCH

This invention was made with government support under Grant No. DP2-OD008530-01 and No. R01 HD075605 awarded by the National Institutes of Health. The government has certain rights in the invention.

FIELD OF INVENTION

The invention disclosed herein generally relates to methods and systems for locating and quantitating molecular targets; e.g., within a cellular environment. Specifically, the invention disclosed herein relates to methods and systems for resolving signals from sequential hybridization interactions. More specifically, the invention disclosed herein relates to methods and systems for dense molecular profiling in single cells by image correlation.

BACKGROUND

Locating and quantitating molecular targets in a cell can be crucial for understanding the functions of such molecules. For example, transcription profiling of cells are essential for many purposes. Microscopy imaging which can resolve multiple mRNAs in single cells can provide valuable information regarding transcript abundance and localization, which are important for understanding the molecular basis of cell identify and developing treatment for diseases.

Currently, two types of interaction-based methods are available for detecting multiple molecule species in cells. The first type relies on simple one color labeling of the molecular species, and repeated hybridization to increase the throughput. For example, an antibody against a particular gene can be labeled with a single dye. Multiple antibodies can be labeled with distinct dyes. Then one can repeatedly hybridize and wash off different sets of antibodies to target increasing amounts of protein species. Recently, it was demonstrated that 60 antibodies can be immunolabeled and quantified in single cells by 12 cycles of hybridization with 5 colors detected in each cycle. See, for example, Micheva and Bruchez, 2012, Current Opinion in Neurobiology, 22(1): 94-100, which is hereby incorporated by reference herein in its entirety.

In particular, hybridization utilizing detection probes capable of generating visual signal has been widely used. For example, fluorescence in situ hybridization (FISH) is a cytogenetic technique that uses probes (e.g., DNA strands) that bind to only those parts of the chromosome with a high degree of sequence complementarity. The DNA strands also include labels capable of rendering fluorescent signals, which is used to detect and localize the presence or absence of specific DNA sequences on chromosomes. Fluorescence microscopy can be used to find out where the fluorescent probe is bound to the chromosomes. FISH is often used for finding specific features in DNA for use in genetic counseling, medicine, and species identification. FISH can be used to detect and localize specific RNA targets (mRNA, lncRNA and miRNA) in cells, circulating tumor cells, and tissue samples. In this context, it can help define the spatial-temporal patterns of gene expression within cells and tissues. However, in complex cellular environment such as intact mammalian cells, it is often difficult to resolve and quantitate visual signals from multiple probes.

The second type method creates barcode labels for the molecular species with multiple fluorophores. It was demonstrated with FISH that up to 32 different transcript species could be detected in parallel; see, for example, Lubeck and Cai, 2012, Nature Methods, 9(7):743-748, which is hereby incorporated by reference herein in its entirety. However, this method is limited to low density molecules in cells because it relies on being able to resolve each molecule spatially to read out the barcode.

What is needed is the art are better methods and systems for analyzing visual signals representing one or more molecular targets even when such targets are present in high density.

SUMMARY OF THE INVENTION

The present invention provides certain insights into challenges or defects associated with existing technologies for profiling transcripts or DNA loci in cells, particularly for single cells. Moreover, the present invention provides new technologies for achieving effective such profiling, including of single cells. Provided technologies are broadly useful, including for example for profiling of isolated cells, cells in tissues, cells in organs, and/or cells in organisms.

For example, the present invention provides the insight that existing technologies such as single cell RNA-seq or qPCR require single cells to be isolated and put into multi-well format, which is a multiple step process that can be cost prohibitive, labor intensive and prone to artifacts. Furthermore, the present invention recognizes that existing in situ sequencing technologies that use enzymatic reactions to convert the mRNA into a DNA template first can be highly inefficient (for example in the mRNA to DNA conversion process), so that, often, only a small fraction of the RNAs are converted and detected. The present invention provides the particular insight that one major downside of such low efficiency, which is estimated at 1% for RT and 10% for PLA, is that it can introduce significant noise ad bias in the gene expression measurements. The present invention further recognizes that existing spectral mRNA barcoding technologies that utilize single molecule fluorescence in situ hybridization (smFISH) require distinct fluorophores for scale up, and may be limited in the number of barcodes that can be generated. smFISH also requires splitting probes into barcoding subsets during hybridization. Because smFISH often uses two or more colors for a target, it produces high density of objects in the image, which can increase the complexity of data analysis.

Among other things, the present inventions provides new technologies for profiling, for example, transcripts and/or DNA loci, that overcome one or more or all of the problems associated with methods prior to the present invention. In some embodiments, the present invention provides methods for detecting multiple targets, e.g., transcripts or DNA loci, in a cell through a sequential barcoding scheme that permits multiplexing of different targets.

In one aspect, provided herein is a method of determining an abundance level of a molecular target within a defined region in a cell. The method comprises the steps of identifying, in the defined region in the cell, a copy of the molecular target by spatially correlating visual data from a plurality of hybridizations $\{1, 2, \ldots N\}$, and determining an abundance level of the molecular target based on a correlation function between the visual data for the first round of hybridization and the visual data for the second round of hybridization.

In some embodiments, N is equal or greater than 2. In some embodiments, the plurality of hybridizations comprises: a first round of hybridization during which a first plurality of probes is applied to the cell. Here, the first plurality comprises one or more first probes interacting with the molecular target to provide a first visual signal at least partially constituting the visual data for the first round of hybridization; and a second round of hybridization during which a second plurality of probes is applied to the cell.

In some embodiments, the second plurality comprises one or more second probes interacting with the same copy of the molecular target to provide a second visual signal constituting the visual data for the second round of hybridization. In some embodiments, the second visual signal differs from the first visual signal.

In some embodiments, the visual data comprise one or more images of the defined region of the cell for each round of hybridization. In some embodiments, one or more images each has predetermined pixel values.

In some embodiments, the method disclosed herein is applicable for analyzing images including a high density of the molecular target. In some embodiments, the images are obtained from conventional microscopy. In some embodiments, the images are obtained from high resolution microscopy. In some embodiments, the defined regions has a density of the molecular target of at least 0.5 to 10 molecules per $\mu m^2$.

In some embodiments, the molecular target is at a density of 0.5 molecule per $\mu m^2$ or higher. In some embodiments, the molecular target is at a density of 1 molecule per $\mu m^2$ or higher. In some embodiments, the molecular target is at a density of 10 molecules per $\mu m^2$ or higher.

In some embodiments, the defined region in the cell is the entire cell. In some embodiments, the defined region in the cell comprises a portion of the cell.

In some embodiments, the molecular target is selected from the group consisting of a nucleic acid molecule, a DNA, an RNA, an mRNA, a protein, a lipid, a carbohydrate, and combinations thereof.

In some embodiments, the method further comprises a step of applying the first plurality of probes to the cell.

In some embodiments, the method further comprises a step of applying the second plurality of probes to the cell after the first plurality of probes is removed from the cell.

In some embodiments, the method further comprises the steps of: locating, in the visual data for the first round of hybridization, a first visual signal within the define region; and identifying, in the visual data for the second round of hybridization, a second visual signal within the define region, wherein the first and second visual signal correspond to the same molecular target.

In some embodiments, the second round of hybridization takes place after the first plurality of probes from the first round of hybridization has been removed from the cell.

In some embodiments, the correlation function between the visual data for the first round of hybridization and the visual data for the second round of hybridization is determined in spatial domain or Fourier domain.

In some embodiments, the visual data comprise: a first image A of the defined region for the first round of hybridization with predetermined pixel values; and a second image B of the defined region for the second round of hybridization with predetermined pixel values.

In some embodiments, the copy of the molecular target is identified in the first image as (x1, y1) and in the second image as (x2, y2), where x1, y1, x2 and y2 are image dimensions in x axis and y axis, respectively.

In some embodiments, the correlation function between the first image A and second image B is:

$$C(k, l) = \sum_{m=0}^{M-1} \sum_{n=0}^{N-1} A(m, n) \cdot B(m-k, n-l), \quad (i)$$

where M and N are dimensions of images in x axis and y axis, respectively, A and B are the images, C is the correlation matrix with k and l as the spatial lag variables;

$$C(i, j) = F^{-1}\{F(A(m, n))F^*(B(m, n))\}, \quad (ii)$$

where F is the Fourier transform operation, M and N are dimensions of images in x axis and y axis, respectively, A and B are the images, and C is the correlation matrix with i and j as the spatial lag variables; or $$G(i, j) = \frac{F^{-1}\{F(A(m, n))F^*(B(m, n))\}}{\langle A(m, n)\rangle\langle B(m, n)\rangle} - 1, \quad (iii)$$

where F is the Fourier transform operation, M and N are dimensions of images in x axis and y axis, respectively, A and B are the images, and G is the correlation matrix with i and j as the spatial lag variables, which has been normalized.

In some embodiments, the abundance level is $$\langle N_{12}\rangle = \frac{G_{12}(0,0)}{G_{11}(0,0)G_{22}(0,0)},$$

where $G_{12}(0,0)$ is the amplitude of the cross-correlation of hyb 1 and hyb 2 images, $G_{11}(0,0)$ is the autocorrelation amplitude of the first hyb image, and $G_{22}(0,0)$ is the autocorrelation amplitude of the second hyb image.

In some embodiments, the plurality of hybridizations $\{1, 2, \ldots N\}$ further comprises: a third round of hybridization during which a third plurality of probes is applied to the cell. In some embodiments, the second plurality comprises one or more third probes interacting with the same copy of the molecular target to provide a third visual signal constituting the visual data for the third round of hybridization. In some embodiments, the third visual signal differs from the first and second visual signals.

In some embodiments, the correlation function is computed based on the visual data for the first round of hybridization, the visual data for the second round of hybridization, and the visual data for the third round of hybridization.

In some embodiments, the method further comprises a step of applying the third plurality of probes to the cell after the first plurality of probes and second plurality of probes are removed from the cell.

In some embodiments, the method further comprises the steps of: identifying a central region of each image, wherein the central region includes the correlation amplitude; and applying background averaging by summing all pixel values on each image except those within the central region.

In some embodiments, the method further comprises a step of: applying to each image of the one or more images, an image filter selected from the group consisting of deconvolution, deblurring, N-D filtering of multidimensional images, 2-D Gaussian filtering of images, 3-D Gaussian filtering of 3-D images, creating predefined 2-D filter, guided filtering of images, normalized 2-D cross-correlation, 2-D adaptive noise-removal filtering, 2-D median filtering, 2-D order-statistic filtering, local standard deviation of image, local range of image, local entropy of grayscale image, general sliding-neighborhood operations, extracting objects from binary image by size, extracting objects from binary image using properties, Pad array, 2-D frequency response, 2-D FIR filter using frequency sampling, 2-D FIR filter using frequency transformation, 2-D FIR filter using 1-D window method, 2-D FIR filter using 2-D window method, 2-D convolution matrix and combinations thereof.

In one aspect, provided herein a method of determining an abundance level of a molecular target within a plurality of defined regions in a cell. The method comprises the steps of identifying, in each defined region in the plurality of defined regions, a copy of the molecular target within the cell by spatially correlating visual data from a plurality of hybridizations $\{1, 2, \ldots N\}$, and determining an abundance level of the molecular target for each defined region in the plurality of defined regions, based on a correlation function between the visual data for the first round of hybridization and the visual data for the second round of hybridization.

In some embodiments, N is equal or greater than 2.

In some embodiments, the plurality of hybridizations comprises: a first round of hybridization during which a first plurality of probes is applied to the cell. Here, the first plurality comprises one or more first probes interacting with the molecular target to provide a first visual signal at least partially constituting the visual data for the first round of hybridization.

In some embodiments, the plurality of hybridizations also comprises: second round of hybridization during which a second plurality of probes is applied to the cell, Here, the second plurality comprises one or more second probes interacting with the same copy of the molecular target to provide a second visual signal constituting the visual data for the second round of hybridization. In some embodiments, the second visual signal differs from the first visual signal.

In some embodiments, the method further comprises a step of assigning a color scheme to each abundance level of the molecular target for each defined region in the plurality of defined regions and creating a color representation of distribution of the molecular target within the cell.

In some embodiments, the molecular target is selected from the group consisting of a nucleic acid, an mRNA, a protein, a lipid, a carbohydrate, and combinations thereof.

In some embodiments, at least one of the plurality of defined regions has a density of the molecular target of at least 0.5 to 10 molecules per $\mu m^2$.

In some embodiments, a computer program product is used for implementing any methods disclosed herein.

It will be understood that any embodiments from any aspect, where applicable, can be used in combination with other embodiments.

BRIEF DESCRIPTION OF THE DRAWINGS

Those of skill in the art will understand that the drawings, described below, are for illustrative purposes only. The drawings are not intended to limit the scope of the present teachings in any way.

FIG. 2A illustrates sequential labeling over N hybridizations followed by the cross-correlation analysis.

FIG. 2B illustrates that molecule A is barcoded by color sequence of R-G-B- . . . -O corresponding to the Cy3, Alexa 594, Alexa 488 . . . and Cy5 images at each round of hybridizations.

FIG. 3A illustrates an exemplary workflow of image correlation based multiplexing and quantification of many molecules in single cells, showing Two subsequent labeling of hyb 1 and hyb2.

FIG. 3B illustrates an exemplary correlation function.

FIG. 3C illustrates an exemplary embodiment in which image filtering is applied to improve the noise of detection.

FIG. 3D illustrates an exemplary embodiment in which cropping is carried out around the highest correlation values.

FIG. 3E illustrates an exemplary embodiment in which image correlation is converted to molecule abundances in a multiplexed fashion up to the Nth order.

FIG. 4A illustrate an exemplary embodiment of correlation FISH technique, showing a schematic of sequential hybridizations of dense mRNA molecules in a cell.

FIG. 4B illustrate an exemplary embodiment of correlation FISH technique, showing individual RNA species are barcoded from multiple hybridizations. Correlation analysis of any two subsets of hybridization images reveals the amount of common RNA molecules. Hyb 1 and Hyb 2 images share the RNA A in the presence of other uncorrelated RNA B and C in each channel.

FIG. 4C illustrate an exemplary embodiment of correlation FISH technique, showing Hyb 2 and Hyb3 cover mutual RNA B molecules with other RNA A and D. Pair-wise correlations across Hybs (1,2) and (2,3) peak values are estimators of the copy number of RNA A (NA) and B (NB), respectively in that cell.

FIG. 4D illustrate an exemplary embodiment of correlation FISH technique, showing Hyb 2 and Hyb3 cover mutual RNA B molecules with other RNA A and D. Pair-wise correlations across Hybs (1,2) and (2,3) peak values are used to compute abundance levels of RNA A and RNA B.

FIG. 5A illustrates an exemplary embodiment, showing a digital cell image with a size of 180×180 pixels. 1,000 A molecules and 1,000 B molecules were randomly distributed within this cell.

FIG. 5B illustrates an exemplary embodiment, showing that positions of A, B, C molecules were convolved or blurred with the PSF of a microscope to mimic the FISH experiments for first hyb. First hyb and second hyb had only common 1,000 A molecules, but 1,000 B and C molecules were uncorrelated.

FIG. 5C illustrates an exemplary embodiment, showing positions of A, B, C molecules were convolved or blurred with the PSF of a microscope to mimic the FISH experiments for second hyb. First hyb and second hyb had only common 1,000 A molecules, but 1,000 B and C molecules were uncorrelated.

FIG. 5D illustrates an exemplary embodiment, showing cross-correlation of first and second hyb images provided this correlation function with a Gaussian in the center of the correlation result.

FIG. 5E illustrates an exemplary embodiment, showing that the background was averaged.

FIG. 5F illustrates an exemplary embodiment, showing that cross-section of the Gaussian in the correlation image was plotted to subtract the peak value from background.

FIG. 5G illustrates an exemplary embodiment, showing that the common number of A molecules was 1,000 (expected: bar 1) and correlation function provided shared molecules in between hybs (calculated: bar 2). Two bars agreed very well without significant error.

FIG. 6A illustrates an exemplary embodiment, showing a digital cell image with a size of 180×180 pixels. 1,000 A molecules and 50,000 B molecules were randomly distributed within this cell.

FIG. 6B illustrates an exemplary embodiment, showing that positions of A, B, C molecules were convolved or blurred with the PSF of a microscope to mimic the FISH experiments for first hyb. First hyb and second hyb had only common 1,000 A molecules, but 1,000 B and C molecules were uncorrelated.

FIG. 6C illustrates an exemplary embodiment, showing positions of A, B, C molecules were convolved or blurred with the PSF of a microscope to mimic the FISH experiments for second hyb. First hyb and second hyb had only common 1,000 A molecules, but 1,000 B and C molecules were uncorrelated.

FIG. 6D illustrates an exemplary embodiment, showing cross-correlation of first and second hyb images provided this correlation function with a Gaussian in the center of the correlation result.

FIG. 6E illustrates an exemplary embodiment, showing that the background was averaged.

FIG. 6F illustrates an exemplary embodiment, showing that the cross-section of the Gaussian in the correlation image was plotted to subtract the peak value from background.

FIG. 6G illustrates an exemplary embodiment, showing that the common number of A molecules was 1,000 (expected: bar 1) and correlation function provided shared molecules in between hybs as around 1,100 (calculated: bar 2). Two bars agreed decently with 10% error.

FIG. 7A illustrates an exemplary embodiment, showing a digital super resolution cell image with a size of 180×180 pixels. 1,000 A molecules and 30,000 B molecules were randomly distributed within this cell.

FIG. 7B illustrates an exemplary embodiment, showing that positions of A, B, C molecules were NOT convolved with the PSF for first hyb. Instead, a super resolution microscope was assumed to create the FISH experiments undoing the effect of PSF blurring. First hyb and second hyb had only common 1,000 A molecules, but 30,000 B and C molecules were uncorrelated.

FIG. 7C illustrates an exemplary embodiment, showing that positions of A, B, C molecules were NOT convolved with the PSF for second hyb. Instead, a super resolution microscope was assumed to create the FISH experiments undoing the effect of PSF blurring. First hyb and second hyb had only common 1,000 A molecules, but 30,000 B and C molecules were uncorrelated.

FIG. 7D illustrates an exemplary embodiment, showing cross-correlation of first and second hyb images provided this correlation function with a Gaussian in the center of the correlation result.

FIG. 7E illustrates an exemplary embodiment, showing that the background was averaged.

FIG. 7F illustrates an exemplary embodiment, showing that the cross-section of the Gaussian in the correlation image was plotted to subtract the peak value from background.

FIG. 7G illustrates an exemplary embodiment, showing that the common number of A molecules was 1,000 (expected: bar 1) and correlation function provided shared molecules in between hybs (calculated: bar 2). Two bars agreed very well without significant error.

FIG. 7H illustrates an exemplary embodiment, showing the cross section of the peak value of correlation showing a single pixel spike rather than a Gaussian functional form.

FIG. 7I illustrates an exemplary embodiment, showing the bar plot between the expected emitters and the calculated emitters.

FIG. 10A illustrates exemplary embodiment, showing effect of non-colocalizing molecules on the detection of colocalizing molecules across two image sequences. Here, a schematic of a cell was shown with a hypothetical RNA1 distribution that is commons in between hyb1 and hyb2. Other sub-regions covering RNA2 and RNA3 molecules do not share common locations.

FIG. 10B illustrates exemplary embodiment, showing simulated images of RNA1-3 molecules from 1,000 to 80,000 molecule range.

FIG. 10C illustrates exemplary embodiment, showing a plot to evaluate the success rate in detection of co-localized molecules in the existence of other noncolocalized molecules across hybridizations. RNA 1 or Molecule 1 was kept constant as the numbers of other molecules were increased by up to 10 folds. n=3 different runs have been processed for each data point. The constant values of RNA1 were 10,000 or 20,000 or 30,000 or 40,000 or 50,000 or 60,000 or 70,000 molecules. For each value of RNA1, the numbers of RNA2 and RNA 3 were increased from 10,000 to 80,000. Along the line direction RNA1 should stay constant in the existence of other non-colocalizing molecules.

FIG. 18A illustrates an exemplary embodiment, showing performance comparison of correlation and localization processing methods at various transcript densities. Correlation achieves much higher density calculations while localization fails to quantitate with increasing transcripts. Up to 20,000 counts or 2 molecule per μm2 density shared A transcripts were measured with both approaches in simulated images in the presence of up to uncorrelated RNA B and C species in two subsequent hybridization. Here, RNA counts were analyzed at the ratio of the A and B/C of 5:1.

FIG. 18B illustrates an exemplary embodiment, showing that RNA density was analyzed at the ratio of the A and B/C of 5:1.

FIG. 18C illustrates an exemplary embodiment, showing that, RNA counts were analyzed at the ratio of the A and B/C of 2:1.

FIG. 18D illustrates an exemplary embodiment, showing that RNA density was analyzed at the ratio of the A and B/C of 2:1.

FIG. 18E illustrates an exemplary embodiment, showing that, RNA counts were analyzed at the ratio of the A and B/C of 1:2.

FIG. 18F illustrates an exemplary embodiment, showing that RNA density was analyzed at the ratio of the A and B/C of 1:2.

DETAILED DESCRIPTION

Definitions

Figure 1A:
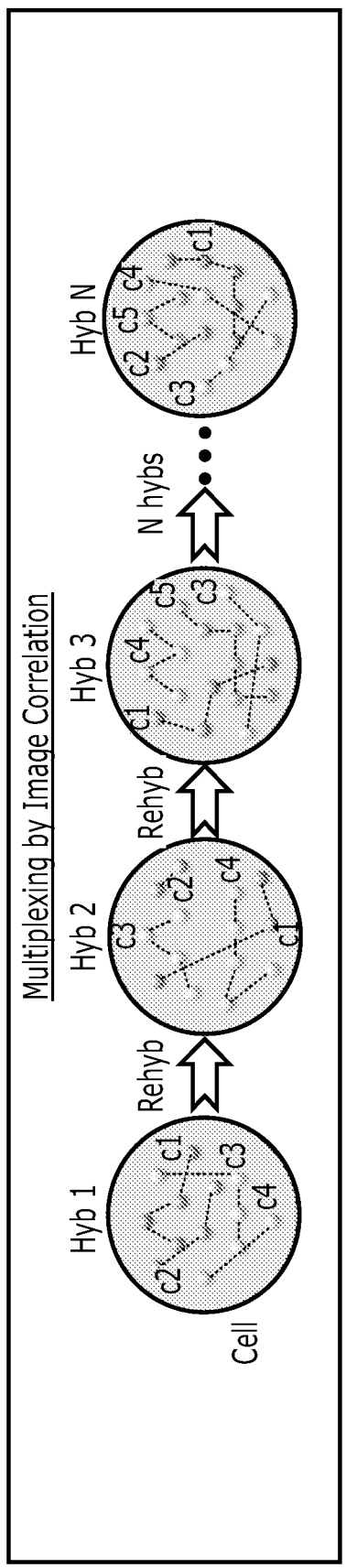
FIG. 1A illustrates Multiplexing by sequential hybridizations of the multiple distinct color labels targeting molecules. F is the number of distinct colors and N is the number of hybridizations enabling $F^N$ multiplex detection of molecules.

Unless otherwise noted, terms are to be understood according to conventional usage by those of ordinary skill in the relevant art.

As disclosed herein, the term "hybridization" generally refers to a phenomenon in which an exogenously added probe binds to specific target sites within a molecular target within a cellular or non-cellular environment. For example, in some embodiments, probes are added to intact cells. In such embodiments, hybridization can be used to both locate and quantitate a molecular target. In some embodiments, probes are added to a mixture of molecular targets from cellular extract.

As disclosed herein, the term "hybridization" generally refers to any identifiable molecular component in a cell, including but not limited to a nucleic acid such as a DNA, an RNA or a tRNA, a protein, a lipid, a carbohydrate, and combinations thereof.

As disclosed herein, the term "probe" generally refers to a molecule that can recognize and bind to specific target sites within a molecular target in a cell. For example, a probe can be a fragment of nucleic acids that can bind to complementary sequence in a target DNA or RNA molecule. In some embodiments, the sequence of the probe is completely complementary to a target sequence. In some embodiments, the sequence of the probe is partially complementary to a target sequence. In some embodiments, a probe can be a protein molecule such as an antibody or a fragment thereof that recognize a specific site in a molecular target such as a phosphorylation site in a protein, a lipid or carbohydrate modified site in a protein, a fragment of specific protein sequence, a specific protein configuration, a specific lipid or carbohydrate configuration, and etc. As disclosed herein, a probe further includes a detectable label.

As disclosed herein, the term "label" generally refers to any moiety in a probe that can generate an indicia to indicate the location and/or quantity of the molecular target. In some embodiments, the indicia is a visual signal such as a fluorescent signal. In some embodiment, the indicia can be a radioactive signal. Exemplary labels for nucleic acids include but are not limited to Alexa 532, 594, Cy5 and Cy7, As disclosed herein, the term "barcode" generally refers to a series of signals produced by probes recognizing the same molecular target during different rounds of hybridization. The order by which the signals are produced create a unique barcode that can be used to identify the molecular target. Exemplary barcodes include a plurality of fluorescent colors that can be detected and resolved by high resolution microscopes.

In one aspect, disclosed herein are methods for analyzing visual data from hybridization interactions in order to more accurately and efficiently locating and quantitating molecular targets within a cellular environment.

As disclosed herein, a hybridization interaction utilizes an exogenously added probe to bind to specific target sites within a molecular target within a cellular or non-cellular environment. Any molecular target that can be recognized by such hybridization interaction is within the scope of the disclosure. Exemplary molecular targets include but are not limited to a nucleic acid molecule (such as a DNA, an RNA, an mRNA and etc.), a protein, a lipid, a carbohydrate or a combination thereof.

Probes vary depending on the molecular targets. A probe includes at least two moieties: a recognition moiety for recognizing the molecular target and a detectable moiety for providing a detectable signal. Exemplary probes include but are not limited to nucleic acid probes, peptides probes, lipid probes, carbohydrate probes, probes of chemical conjugates, and combinations thereof. Exemplary detectable signals include but are not limited to a fluorescent signal, a radioactive signal, or a dye.

In some embodiments, for example, in fluorescence in situ hybridization (FISH), strands of nucleic acid sequence are used to identify specific target sites on chromosomes. In some embodiments, the oligonucleotide probes encode recognition sequences that are complementary or mostly complementary to sequences of the target sites. Similar types of probes are used to identify target sites in DNA or RNA transcripts.

In some embodiments, peptide probes can be used to recognize specific sites in a molecular target such as a protein, a lipid, a carbohydrate or a combination thereof. For example, an antibody analog can be used to recognize specific sites within a protein target, such as a phosphorylation site.

In some embodiments, a probe comprises one detectable moiety. In some embodiments, a probe comprises two or more detectable moieties.

In some embodiments, multiple probes are used for the same molecular target to increase signal intensity. In some embodiments, each of the multiple probes targeting the same molecular target interacts with a different portion of the target. In some embodiments, multiple probes for a target are positioned in proximity to each other on the target.

In some embodiments, probes for a molecular target are positioned within a targeted region of the target. A targeted region can have various lengths. For example, a targeted region in a nucleic acid target can include about 20 bp, about 30 bp, about 40 bp, about 50 bp, about 60 bp, about 80 bp, about 100 bp, about 150 bp, about 200 bp, about 250 bp, about 300 bp, about 350 bp, about 400 bp, about 450 bp, about 500 bp, 600 bp, about 700 bp, about 800 bp, about 900 bp, about 1,000 bp in length.

In some embodiments, all probes for a molecular target have the same detectable moieties. In some embodiments, all probes are labeled in the same way. In some embodiments, all probes for the same molecular target have the same fluorophore.

As disclosed herein, a series of signals produced by different probes recognizing the same molecular target during different rounds of hybridization can create a unique barcode specific for the molecular target. The order by which the signals are produced can be used to uniquely identify the molecular target. For example, in three rounds of hybridization, three sets of probes are used to identify three different molecular targets A, B and C. In the first round of hybridization, probes recognizing molecule A produce a red signal. In the second round of hybridization, probes recognizing molecule A produce a green signal. In the third round of hybridization, probes recognizing molecule A produce a yellow signal. As such, the barcode encoding molecule A is R-G-Y; i.e., when examining images from the three rounds of hybridization, a position wherein molecule A is located in the cell will show red in the image for the first round of hybridization, green in the image for the second round of hybridization, and yellow in the image for the second round of hybridization. A barcode is determined by the signals produced by detectable labels in the probes and the order by which different rounds of hybridization are applied. Similarly, barcodes for molecular targets B and C can be G-Y-R and Y-R-G, respectively.

In order to avoid interference and misinterpretation of barcodes, it is important to removes probes from an earlier round of hybridization before applying a new set of probes for a later round of hybridization.

Detailed disclosure concerning exemplary probes, detectable labels, and barcoding schemes can be found in US Patent Publication No. 2014/0031243 and International Publication No. WO/2014/182528, each of which is hereby incorporated by reference herein in its entirety.

Methods and systems disclosed herein can be applied to analyzing images where probes bearing different signals are used to identify one or more molecular targets during different rounds of hybridization interactions.

In some embodiments, the methods disclosed herein are applied to analysis of high resolution images obtained from multiplexing hybridizations; for example, those disclosed in US Patent Publication No. 2014/0031243 and International Publication No. WO/2014/182528, each of which is hereby incorporated by reference herein in its entirety.

Figure 1B:
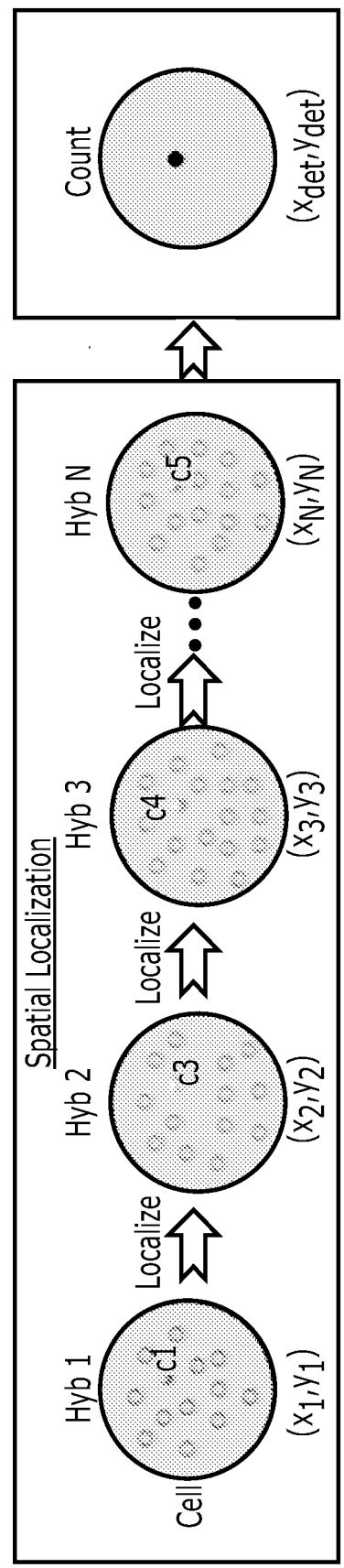
FIG. 1B illustrates spatial localization ($x_i, y_i$ where i=1 to N) of molecules across hybridizations yields color barcode sequence for each molecule specie. The detected molecules (xdet, ydet) are summed to compute the copy number in each cell.
Figure 1C:
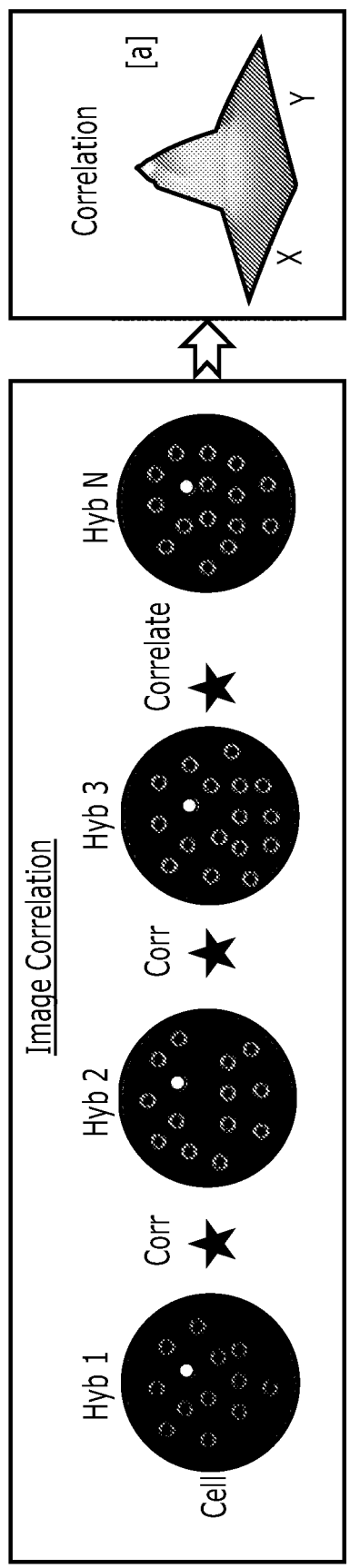
FIG. 1C illustrates a simple cross-correlation of the images across hybridizations provides a correlation function. The depth of the correlation [a] is converted to the abundance of molecules.

FIGS. 1A through 1C illustrate an exemplary embodiment of multiplexing analysis in which probes with 4 different colors are used to identify and extract the abundance of a large number of molecular targets using sequential hybridization (FIG. 1A). Each molecular species, mRNA or protein, can be labeled with FISH probes or antibodies. At each round of hybridization, the probe is labeled with a distinct dye. Thus, each species is now barcoded by the sequence of dyes at the different rounds of hybridization and imaging. Spatial localization of molecules across sequential hybridizations provides the color barcode sequences for each molecular species (FIG. 1B). FIG. 1C illustrates that cross-correlation of the images corresponding to the barcode can reveal the abundances of the molecules.

Referring to FIG. 1A, an image representing the first round of hybridization interactions (Hyb 1) is shown. Each dot represent a molecular target where the same colored dots represent the same molecular target. For clarity, dots of the same color are linked by a dashed line. For example, in the Hyb 1 image, there are four dots of color 1 (c1: e.g., red), three dots of color 2 (c2: e.g., purple), four dots of color 3 (c3: e.g., green) and two dots of color 4 (c4: e.g., blue). In the Hyb 2 image, there are three c1 dots, two c2 dots, four c3 dots and five c4 dots. In the Hyb 3 image, there are four c1 dots, no c2 dots, three c3 dots, four c4 dots and six c5 (orange) dots. In the Hyb 3 image, there are four c1 dots, three c3 dots, four c4 dots, and six c5 dots. Similarly, in the Hyb N image, there are five c1 dots, two c2 dots, three c3 dots, three c4 dots, and three c5 dots.

FIG. 1B illustrates an exemplary embodiment of spatial localization. Here, different dots representing the same molecular target (molecule A) are identified in images Hyb 1, Hyb 2, Hyb 3, . . . and Hyb N are identified as $(x_i, y_i)$, where i=1 to N; i.e., $(x_1, y_1)$, $(x_2, y_2)$, $(x_3, y_3)$, . . . and $(x_N, y_N)$. In some embodiments, the values of $(x_i, y_i)$ are determined based on the pixel dimensions of an image. For example, in an image of X pixels by Y pixels, c1 dot in the Hyb 1 image is located at $x_i$th pixel in one dimension and $y_i$th pixel in the other dimension. When the position of the cell being analyzed remains unchanged cross different images (Hyb 1, Hyb 2, Hyb 3, . . . and Hyb N), positions representing molecule A (e.g., c1 dot in Hyb 1, c3 dot in Hyb 2, c4 dot in Hyb 3, . . . c5 dot in Hyb N) can be cross-correlated. The order by which these dot appear and their respective colors provides a unique barcode representing molecule A. In this case, the barcode is red(R)-green (G)-blue(B)- . . . -orange(O) or R-G-B- . . . -O. Applying the analysis to each image, the detected molecules $(x_{det}, y_{det})$ are summed to compute the copy number in each cell.

Previously, it was required that individual molecular targets be resolved in the images; i.e., the targets must be of low density. Referring to FIG. 1C, the method disclosed herein does not require individual mRNA or protein to be resolved in the image. A simple cross-correlation of the images across hybridizations provides a correlation function. The depth of the correlation [a] is converted to the abundance of molecules. As the multiplex capacity of sequential barcoding scales as $F^N$, where F is the number of fluorophore channels and N is the rounds of hybridizations. A large number of molecules can be multiplexed, as F is typically 6 and N can be as high as 10 corresponding to $6^6$=46656.

In some embodiments, the method disclosed herein is applicable for analyzing images including a high density of the molecular target. In some embodiments, the images are obtained from conventional microscopy. In some embodiments, the images are obtained from high resolution microscopy. In some embodiments, in a defined region being analyzed, the molecular target is at a density of 0.5 molecule per µm² or higher, 1 molecule per µm² or higher, 1.5 molecules per µm² or higher, 2 molecules per µm² or higher, 3 molecules per µm² or higher, 4 molecules per µm² or higher, 5 molecules per µm² or higher, 6 molecules per µm² or higher, 7 molecules per µm² or higher, 8 molecules per µm² or higher, 9 molecules per µm² or higher, 10 molecules per µm² or higher, 12 molecules per µm² or higher, 15 molecules per µm² or higher, 20 molecules per µm² or higher, 25 molecules per µm2 or higher, 30 molecules per µm² or higher, 40 molecules per µm² or higher, 50 molecules per µm² or higher, 80 molecules per µm² or higher, 100 molecules per µm² or higher or 200 molecules per µm² or higher.

Figure 2C:
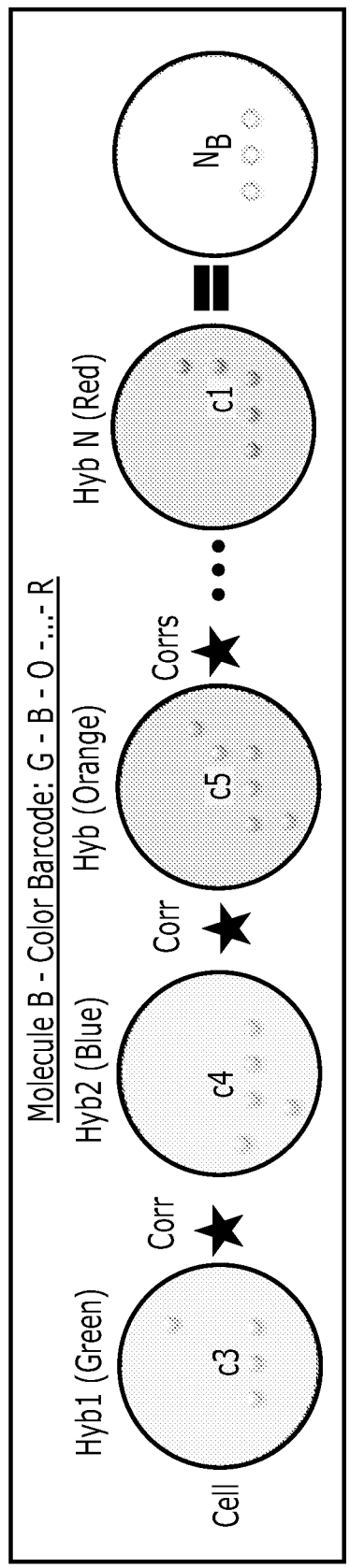
FIG. 2C illustrates that molecule B is barcoded by the sequence of G-B-O- . . . -R corresponding to the Alexa 594, Alexa 488, Cy5 . . . and Cy3 images of the same individual cell.

Barcoding scheme and abundance calculation is further illustrated in FIGS. 2A through 2C, which shows detection of two different molecules using cross-correlation of sequential hybridizations. Colored dots representing two molecular targets (molecules A and B) are highlighted in FIG. 2A. Molecule A (assume mRNA 1) is labeled with Cy3 (Red) in the first round of hybridization, Alexa 594 (Green) in the 2nd round of hybridization, Alexa 488 in the 3rd round of hybridization, and after more hybs, lastly Cy5 (Orange) in the Nth round of hybridization. Then the abundance of mRNA 1 is obtained by the correlation depth or amplitude of the Cy3, Alexa 594, Alexa 488 . . . and Cy5 images at each round of hybridization. Similarly, Molecule B (assume mRNA2) can be measured by the correlation depth of the Alexa 594, Alexa 488, Cy5 . . . and Cy3 images of the same single cell. Here, the barcode for molecule A is R-G-B- . . . -O (FIG. 2B) and the barcode for molecule B is G-B-O- . . . -R (FIG. 2C). Both analyses show the same abundance level; i.e., it is determined there are both three copies of each molecule in the cell.

Figure 3G:
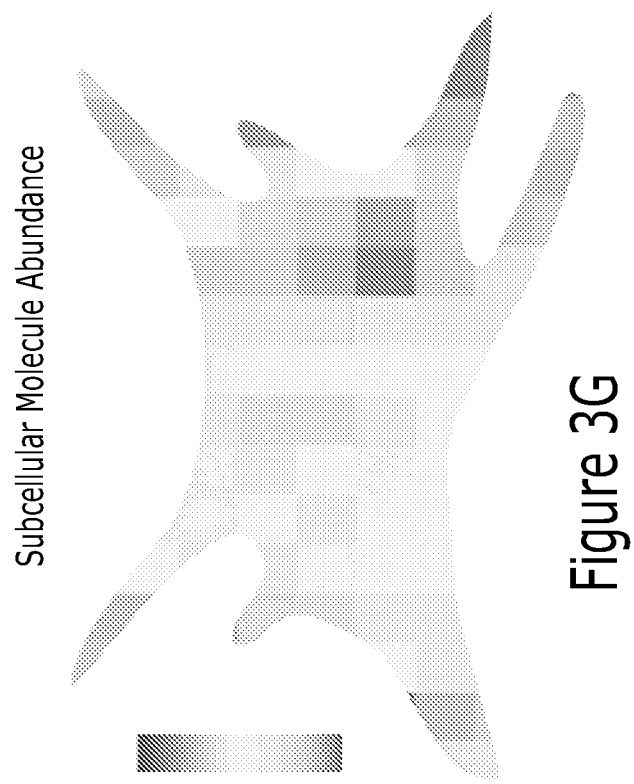
FIG. 3G illustrates an exemplar embodiment, showing subcellular map of molecule abundance is also obtained by applying cross correlation to the subset of the cell image. This approach, with its simplicity, enables multiplexing despite the loss in the spatial resolution of microscopic analysis.
Figure 3F:
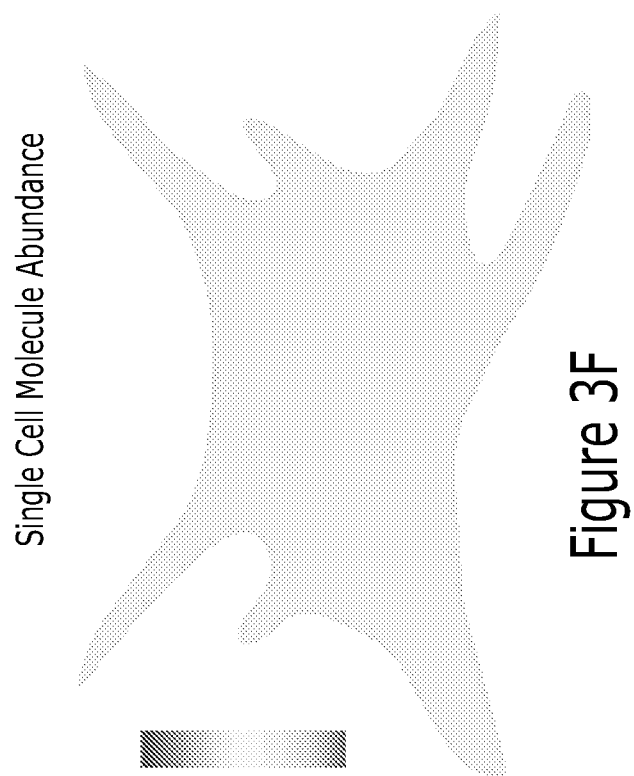
FIG. 3F illustrates an exemplar embodiment, showing the result of cross correlation calculation provides a single cell value of molecule abundance.

FIG. 3 illustrates an exemplary workflow of the correlation algorithm as disclosed herein. FISH or Antibody labeled Images are obtained from a wide field, confocal or TIRF microscopy setup using 60× or 100× single molecule resolution. The same cell is labeled and imaged multiple times with different color dyes targeting same molecules during different rounds of hybridization. Unique color sequences or assigned to specific barcodes corresponding to molecules.

In some situation, cell coordinates might change during the imaging and sample processing. As such, coordinates obtained from different images will differ from each other. For example, between subsequent hybridizations hyb 1 and hyb 2, Xa is not equal to Xm, and/or Yb is not equal to Yn in (FIG. 3A). This is not a concern for image correlation because the amplitude of the correlation is the same strength regardless of its spatial position at $X_{m-a}, Y_{n-b}$ (FIG. 3B). This approach brings simplicity to image processing, because the image registration algorithms are not needed in image correlation calculations.

In some embodiments, additional processing methods such as background averaging and image filtering are used to obtain quantifiable correlation amplitude (FIG. 3C). Even in the high noisy images, correlation amplitude is quantified with 10% error (see simulations section for details). In some embodiments background averaging is just the summation of pixel values other than the central region. In some embodiments, the center portion of the image includes the correlation amplitude.

Exemplary image filtering methods include but are not limited to deconvolution, deblurring and etc. can also be used to improve cross-correlation detection. In some embodiments, image filtering further includes N-D filtering of multidimensional images, 2-D Gaussian filtering of images, 3-D Gaussian filtering of 3-D images, creating predefined 2-D filter, guided filtering of images, normalized 2-D cross-correlation, 2-D adaptive noise-removal filtering, 2-D median filtering, 2-D order-statistic filtering, local standard deviation of image, local range of image, local entropy of grayscale image, general sliding-neighborhood operations, extracting objects from binary image by size, extracting objects from binary image using properties, Pad array, 2-D frequency response, 2-D FIR filter using frequency sampling, 2-D FIR filter using frequency transformation, 2-D FIR filter using 1-D window method, 2-D FIR filter using 2-D window method, 2-D convolution matrix and combinations thereof.

Processing methods can be applied at any step during the process. In some embodiments, the processing method is applied to image data before the correlation result of FIG. 3B is obtained. In some embodiments, the processing method is applied to image data after the correlation result of FIG. 3B is obtained. In some embodiments, the processing methods can be applied at multiple steps in the process.

In some embodiments, the correlation function is then cropped around the highest value of correlation, for example, with a radius of 500 nm by 500 nm, or 1 um by 1 um or 2 um by 2 um area (FIG. 3D). Gaussian function is then fit onto this high-resolution correlation function $G_{12}$ or $G_{21}$.

In some embodiments, the obtained Gaussian form is then evaluated at 0 to measure the correlation depth or amplitude or strength (FIG. 3E).

In some embodiments, this process is repeated for auto-correlation and cross correlation based quantification of molecule abundance in single cells (see the previous theory part for details of calculations).

As disclosed herein, abundance of a molecule in single cells is quantified from image correlations. For example, two approaches are used to perform correlations, one in spatial domain and another in Fourier domain. The spatial domain is implemented by shifting one of the images and multiplying the pixel values to create a correlation matrix (Equation 1).

$$C(k, l) = \sum_{m=0}^{M-1} \sum_{n=0}^{N-1} A(m, n) \cdot \overline{B}(m - k, n - l), \quad \text{(Eqn. 1)}$$

where M and N are dimensions of images in x and y, A and B are the images, C is the correlation matrix with k and l as the spatial lag variables.

Spatial domain method works accurately for image correlation, however, it requires extensive multiplications making it slow processing scheme. Thus, a Fourier domain approach is used to take the Fourier Transform of both images, multiply both images once, and then take inverse transform back to the spatial domain (Equation 2), providing much faster results.

$$C(i,j)=F^{-1}\{F(A(m,n))F^*(B(m,n))\} \quad \text{(Eqn. 2)},$$

where F is the Fourier transform operation, and A and B are the images, and C is the correlation matrix.

To correct for the deviations in the pixel brightness of two images, the image correlation function is normalized and an offset value is subtracted to compute the correlation function (Equation 3):

$$G(i, j) = \frac{F^{-1}\{F(A(m, n))F^*(B(m, n))\}}{\langle A(m, n)\rangle\langle B(m, n)\rangle} - 1 \quad \text{(Eqn. 3)}$$

Autocorrelation of each channel is used to measure to total number of molecules in a given color channel. In Equations 1 to 3, A and B images are taken as the same, as the autocorrelation implies correlation of the image by itself. Inverse of the auto correlation amplitude is then used to compute abundance in each cell (Equation 4).

$$\langle N_N \rangle \approx \frac{1}{G_{NN}(0,0)}, \quad \text{(Eqn. 4)}$$

where N is the index of a color channel in a single labeling experiment. For instance, total number of molecules in two subsequent hybridizations or labeling schemes, corresponding to hyb 1 and hyb2 (FIG. 9), are computed using such autocorrelation measurements (Equation 5).

$$\langle N_1 \rangle \approx \frac{1}{G_{11}(0,0)} \langle N_2 \rangle \approx \frac{1}{G_{22}(0,0)} \quad \text{(Eqn. 5)}$$

The cross-correlation across color channels enables detection of common, shared, and colocalized molecules across these images. For example, the number of common molecules in between hyb1 and hyb2 is measured by using the cross correlation amplitude of images 1 and 2, divided by the multiplication of autocorrelation amplitudes (Equation 6)

$$\langle N_{12} \rangle = \frac{G_{12}(0,0)}{G_{11}(0,0)G_{22}(0,0)}, \quad \text{(Eqn. 6)}$$

A common molecule across many images is also computed using the similar strategy. For 3 hybridizations, the cross correlation of three images are computed and then divided by autocorrelation amplitudes of each images (Equation 7).

$$\langle N_{123} \rangle = \frac{G_{123}(0,0)}{G_{11}(0,0)G_{22}(0,0)G_{33}(0,0)} \quad \text{(Eqn. 7)}$$

Higher order correlations of N images follow the same general scheme of molecule quantification (Equation 8). The amplitude of cross correlations of N images is divided by individual autocorrelation amplitudes.

$$\langle N_{12\ldots N} \rangle = \frac{G_{12\ldots N}(0,0)}{G_{11}(0,0)G_{22}(0,0)\ldots G_{NN}(0,0)}, \quad \text{(Eqn. 8)}$$

It will be understood by one of skill in the art that the correlation and abundance calculation functions are provided as illustration and should not in any way, limit the scope of the disclosure.

Figure 3H:
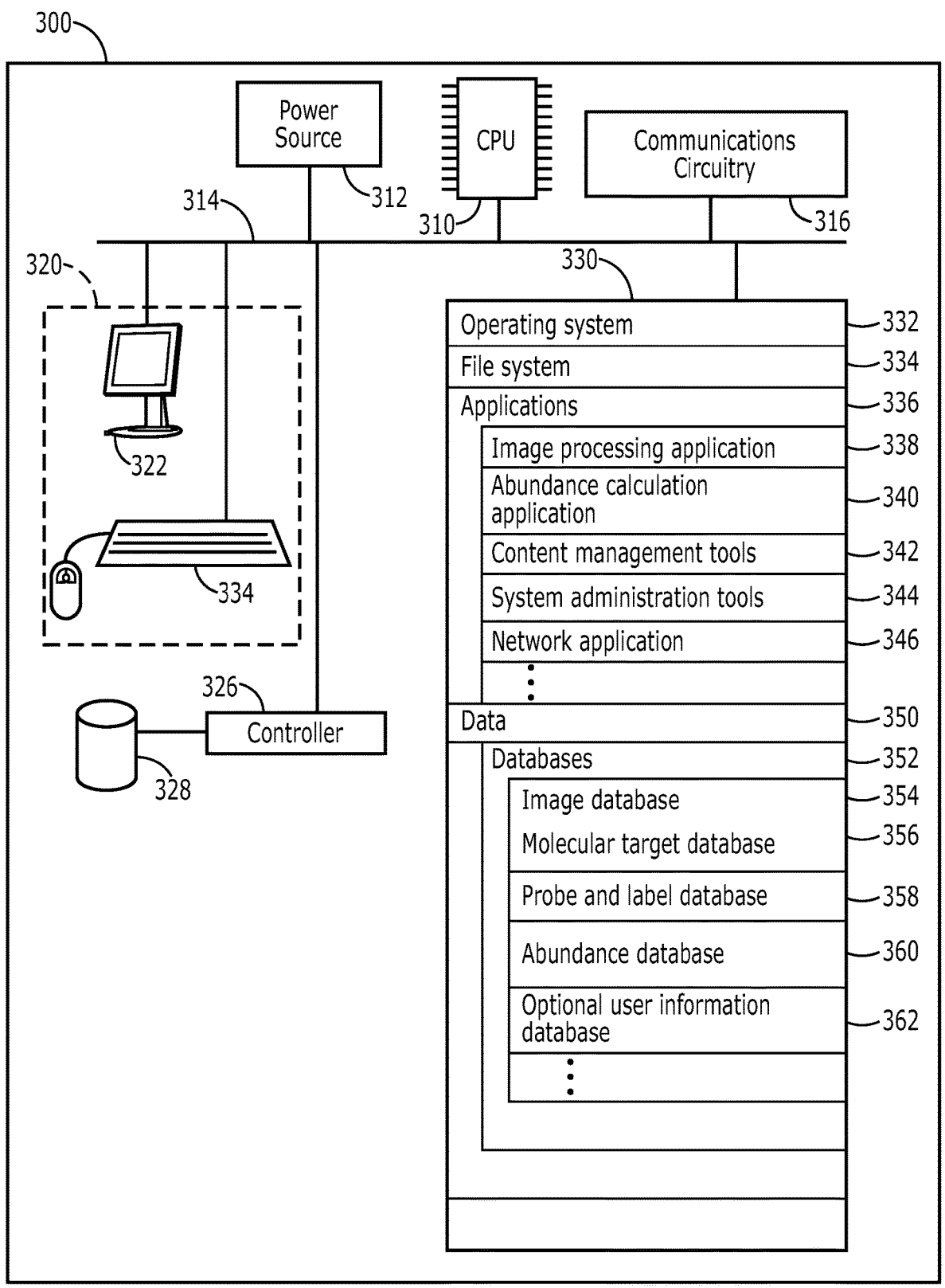
FIG. 3H illustrates an exemplary embodiment computer system.

In one aspect, provided herein is a computer system for implementing the method disclosed herein (see, for example, FIG. 3H).

In some embodiments, a computer system 300 may comprise a central processing unit 310, a power source 312, a user interface 320, communications circuitry 316, a bus 314, a controller 326, an optional non-volatile storage 328, and at least one memory 330.

Memory 330 may comprise volatile and non-volatile storage units, for example random-access memory (RAM), read-only memory (ROM), flash memory and the like. In preferred embodiments, memory 330 comprises high-speed RAM for storing system control programs, data, and application programs, e.g., programs and data loaded from non-volatile storage 328. It will be appreciated that at any given time, all or a portion of any of the modules or data structures in memory 330 can, in fact, be stored in memory 328.

User interface 320 may comprise one or more input devices 324, e.g., keyboard, key pad, mouse, scroll wheel, and the like, and a display 322 or other output device. A network interface card or other communication circuitry 316 may provide for connection to any wired or wireless communications network, which may include the Internet and/or any other wide area network, and in particular embodiments comprises a telephone network such as a mobile telephone network. Internal bus 314 provides for interconnection of the aforementioned elements of computer system 300.

In some embodiments, operation of computer system 300 is controlled primarily by operating system 332, which is executed by central processing unit 310. Operating system 332 can be stored in system memory 330. In addition to operating system 332, a typical implementation system memory 330 may include a file system 334 for controlling access to the various files and data structures used by the present invention, one or more application modules 336, and one or more databases or data modules 350.

In some embodiments in accordance with the present invention, applications modules 336 may comprise one or more of the following modules described below and illustrated in FIG. 3H. The methods and systems are provided by way of illustration only. They should in no way limit the scope of the present invention.

Image Processing Application 338.

In some embodiments, one or more image processing applications are used to carry out spatial correlation. In some embodiments, image processing application 338 also includes the additional image processing algorithm, for example, those for background processing or image filtering.

Abundance Calculation Application 340.

In some embodiments, one or more abundance calculation applications are used to carry out computation and presentation of abundance data. For example, abundance calculation application 340 is used to create the representation in FIGS. 3F and 3G, which illustrate the distribution of selected molecular targets within the cellular environment.

Content Management Tools 342.

In some embodiments, content management tools 342 are used to organize different forms of content databases 352 into multiple databases, e.g., an image database 354, a molecular target database 356, a correlation function database 358, an abundance database 360, and an optional user information database 362. In some embodiments in accordance with the present invention, content management tools 342 are used to search and compare any of the databases hosted on computer system 300. Alternatively, commands can be sent to a remote data server via network application 348 to initiate search and comparison on the remote data server.

The databases stored on computer system 300 or remote data server comprise any form of data storage system including, but not limited to, a flat file, a relational database (SQL), and an on-line analytical processing (OLAP) database (MDX and/or variants thereof). In some specific embodiments, the databases are hierarchical OLAP cubes. In some embodiments, the databases each have a star schema that is not stored as a cube but has dimension tables that define hierarchy. Still further, in some embodiments, the databases have hierarchy that is not explicitly broken out in the underlying database or database schema (e.g., dimension tables are not hierarchically arranged). In some embodiments, the databases in fact are not hosted on remote data server 300 but are in fact accessed by centralized data server through a secure network interface. In such embodiments, security measures such as encryption is taken to secure the sensitive information stored in such databases.

System Administration Tools 344.

In some embodiments in accordance with the present invention, system administration and monitoring tools 344 administer and monitor all applications and data files of computer system 300.

Network Application 346.

In some embodiments, network applications 346 connect a computer system 300 with multiple network services. In some embodiments in accordance with the present invention, upon recognition, a network application 346 receives data from intermediary gateway servers before it transfers the data to other application modules such as image processing application 338, abundance calculation tools 340, and system administration tools 342.

In some embodiments, each of the data structures stored on computer system 300 is a single data structure. In other embodiments, any or all such data structures may comprise a plurality of data structures (e.g., databases, files, and archives) that may or may not all be stored on computer system 300. The one or more data modules 350 may include any number of databases 352 organized into different structures (or other forms of data structures) by content management tools 342.

In addition to the above-identified modules, data 350 may be stored on computer system 300. Such data comprises content databases 352 and user data 362. Exemplary databases 352 include image database 354, molecular target database 356, correlation function database 358, abundance database 360, and optional user information dataset 362, which are described below in more details.

Image Database 354.

Images obtained from different rounds of hybridization interactions are stored in image database 354. In some embodiments, images are digital and include precise pixel information. In some embodiments, images are digitized from non-digital images. In some embodiments, image databased includes the "raw" data image as well as any additional processed images based on the original "raw" image. For example, the processed images include cleaned up images after background averaging and image filtering. In some embodiments, the processed images include multiple images of sub-regions of an original image.

Molecular Target Database 356.

In some embodiments, computer system 300 hosts a molecular target database 356. Different types of molecular targets can be organized by categories; e.g., protein versus nucleic acid. In some embodiments, different molecular targets are organized by their susceptibility to selected probes and detectable labels.

Probe and Label Database 358.

In some embodiments, computer system 300 also includes one or more database with information concerning probes and labels that can be used to identify selected molecular targets.

Abundance Database 360.

In some embodiments, computer system 300 includes an abundance database for storing abundance data. In some embodiments, abundance data are presented in graphic format to illustrate subcellular distribution of selected molecular targets.

Optional User Database 362.

In some embodiments, an optional user database 362 may be created and stored on computer system 300 where a user can save raw, processed or partially processed data.

Profiling molecules such as RNAs or proteins in cells is the key to explore cell identities and can reveal patterns in gene regulatory networks. Here, provided herein is an example of dense transcript profiling in single cells by image correlation decoding.

The ability to barcode a large number of different mRNA species in single cells have been solved by the sequential FISH (seqFISH) method and recently been demonstrated to code for 100-1000 transcripts in single cells. Exciting works in in situ sequencing can also decode the RNA species with nucleotide resolution. In the seqFISH methods, because of the high efficiency of the labeling the RNA molecules, multiplexing a large number of transcripts results in a high-density image that renders the temporal barcode difficult to resolve. It was previously demonstrated that using super resolution microscopy improved the detection of abundant RNA molecules. However, super-resolution microscopy is difficult to implement in thick samples. Thus, a method to resolve the temporal barcode impart by sequential FISH is needed to decode high copy number RNAs.

In one aspect, disclosed herein is an image correlation method for decoding the temporal barcode in seqFISH experiments, termed correlation FISH (corrFISH). The principle is illustrated in FIGS. 4A through 4D.

Here, RNA species are encoded such that each RNA species appear only in two of the hybridizations out of a total of 3 rounds (FIG. 4A). In some embodiments, RNA B appears in round 2 and 3. While there are other RNAs also labeled in round 2 or round 3, no other RNAs are labeled in both round 2 and 3 (FIG. 4B). Thus, only FISH spots that correspond to RNA B are in the same positions between hyb 2 and hyb 3. When the images from hyb 2 and hyb 3 are cross-correlated, only RNA B will generate a positive correlation (FIG. 4C) with an amplitude that is proportional to the number of RNA B molecules (FIG. 4D) while the other RNA species will not be correlated and not contribute to the cross-correlation. Thus, the copy number of RNA B can be extracted from the cross-correlation of the images corresponding to the RNA B barcode assignment even when the images are dense.

The methods and systems disclosed herein can be used localize and quantitate molecular targets within a single cell. For example, overall abundance levels can be determined for molecular targets to indicate their relative expression level (e.g., FIGS. 3F and 3G). Additionally, the cell can be divided into multiple sub-regions and an abundance level can be determined for each sub-region. This way, the method can be used to visualize distribution of certain molecular targets throughout the cell; for example, whether a molecular target is concentrated in the nucleus or cytosol.

In addition, the methods and systems disclosed herein can be used for organelle specific analysis. For example, they can be used to profile nucleic acids from mitochondria. They can also be used to profile transcripts from ribosome. In some embodiments, the methods and systems disclosed herein can be used for RNA-RNA interaction mapping. In some embodiments, they can be used for protein-RNA mapping or protein-protein mapping and etc.

In one aspect, the present invention can be implemented as a computer system and/or a computer program product that comprises a computer program mechanism embedded in a computer readable storage medium. Further, any of the methods of the present invention can be implemented in one or more computers or computer systems. Further still, any of the methods of the present invention can be implemented in one or more computer program products. Some embodiments of the present invention provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer system or a computer program product that contains any or all of the program modules as disclosed herein. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Single Cell Versus Subcellular Molecule Abundance

We have shown by computer simulation that hundreds of molecular species can be multiplexed and their abundances extracted with less than 10% error using this correlation method. This method is applicable to many molecular species, such as mRNA, proteins, lipids and carbohydrates. Each single cell is encoded with a singular value for the abundance of molecules (FIG. 4A). Lastly, the correlation analysis can be applied only on a subset of the image to obtain spatial information within the cell (FIG. 4B). Partitioning the cell into, for example, 20×20 or 40×40 or 80×80 pixels enables sub-region analysis. The abundance map resolution will be lower than the image resolution, and is in a tradeoff with the abundance estimate accuracy. However, one gains the simplicity of implementation and ease of analysis. For example, a 100 protein analysis will only require 3 rounds of h, compared to 20 rounds previously.

Example 2

Methods for Simulations

Point emitters were randomly distributed in a digital image of size 128×128 pixels or 180×180 pixels or 256×256 pixels or 512×512 pixels using a custom written MATLAB algorithm. Emitters were convolved with point-spread function (PSF) of a 100× wide field fluorescence microscope. The obtained images mimic the molecules labeled with fluorescent dyes. Adjusting the total number of emitters per simulation area changed concentration of the molecules. Sequences of these digital images were correlated in spatial or Fourier domains to compute the abundances of molecules that are common across these image arrays. In the correlation process, PSF of the image detection does not need to be evaluated, as the correlation amplitude is the key to obtain molecule copy number. Fixing the position of the cross-correlation term and averaging the background of the rest of the image improved the performance of the molecule detection.

Example 3

Regular Wide Field Microscopic Image Analysis

In the case of regular wide field microscopic image analysis: 180×180 pixels were simulated as a digital image of a cell. Three types of molecules (A, B, and C molecules) were included in the simulations. Molecule A was the target to detect using cross-correlation algorithm. Molecules B and C were additional contaminants in the first and second hybridizations, respectively. FIG. 5A shows randomly distributed 1,000 A and 1,000 B molecules or emitters or single-pixel positions within the simulation window. These molecules were convolved or blurred with the PSF of a microscope creating lower resolution images as illustrated in FIG. 5B-C. In between first hyb and second hyb, only the 1,000 A molecules share the same positions, while 1,000 B and 1,000 C molecules are totally uncorrelated across these two images (FIG. 5B-C). The cross-correlation of the first hyb and second hyb images provided a cross correlation function exhibiting a Gaussian like peak appearing in the central regions of the correlation image (FIG. 5D).

A region of interest (100 by 100 pixels or 200 by 200 pixels) around this peak value was then defined and averaged rest of the image to create a uniform background (FIG. 5E). The peak value cross section obeyed a Gaussian fit to measure the peak pixel value and the average background content. The highest value of this correlation image was subtracted from the averaged background value. This calculation provided the number of A molecules that appeared in both first and second hyb. Thus, expected emitters (number of A molecules that were simulated) and calculated emitters (number of commons molecules across hybs 1 and 2 that were computed using correlation function) were compared in a bar plot in FIG. 5G. These two bar plots showed that the number of A molecules was correctly estimated using correlation approach.

Similar to the FIGS. 5A through 5G, FIGS. 6A through 6G included 1,000 A molecules but much higher 50,000 B and 50,000 C molecules in first and second hyb images. Interestingly, even if the Gaussian function in the center of the correlation function (FIG. 5D) was not clearly observed, the spatial position of the peak value of the correlation was fixed and rest of the image was averaged to make a background value. FIG. 6G presents the detection of 1,000 expected A molecules in the presence of other uncorrelated each 50,000 B and C molecules in hybs 1 and 2 respectively. Bar plot revealed about 1,100-1,200 A molecules from correlation calculation while the expected number of A molecules was around 1,000. This shows about 10% error in the calculations. Considering the density of these objects, this is fairly good estimate for single cell applications.

Example 4

Super Resolution Microscopic Image Analysis

In previous section, correlation analyses were applied to wide field microscopic images. Correlation can also be applied to super resolution images. Super resolution method can undo the PSF blurring effect of a microscope to increase the resolution of the microscopic images. Thus, we ignored the PSF in the next simulations. Rest of the analyses was kept the same. FIG. 7A through 7I show simulation of 1,000 A molecules and uncorrelated 30,000 each B and C molecules. FIGS. 7A and 7B were the same as the PSF was omitted from the analysis. FIG. 7D was the raw correlation image and 7E was the background averaged one. FIGS. 7F and 7G were the zoomed versions of D and E respectively. The current peak value of correlation was a single pixel rather than a Gaussian functional form. The cross section of this peak shows a single pixel spike for the highest value in FIG. 7H. The bar plot in FIG. 7I showed the excellent agreement with expected 1,000 molecules and the calculated 1,000 A molecules from super resolution images.

Figures 8A, 8B, 8C, 8D, 8E, 8F, 8G:
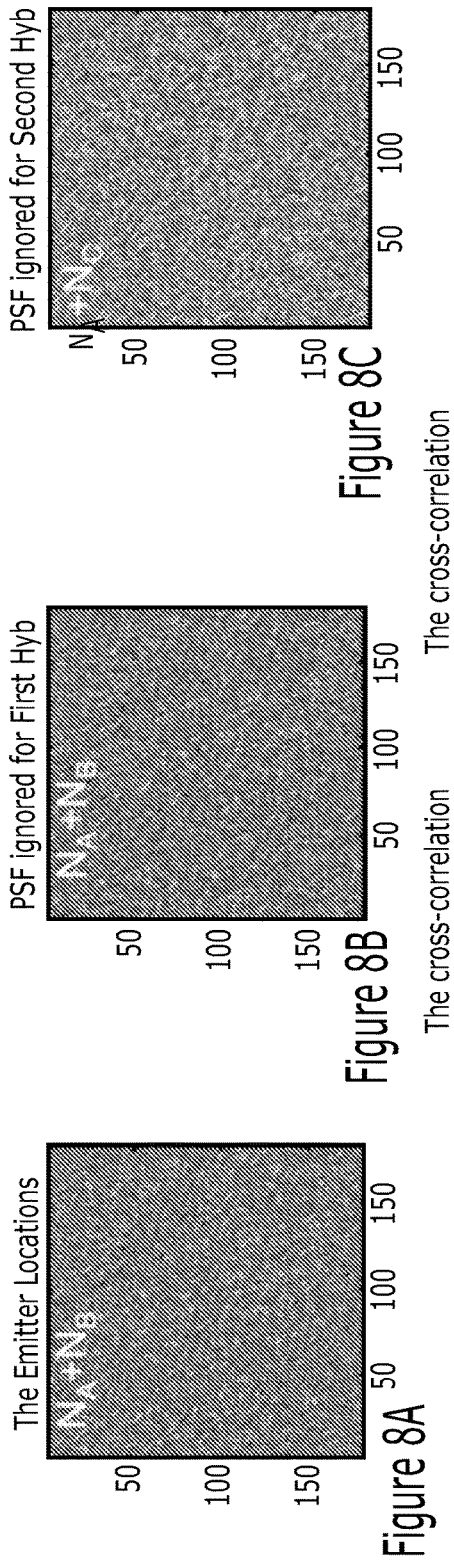
FIG. 8A illustrates an exemplary embodiment, showing a Digital super resolution cell image with a size of 180×180 pixels. 20,000 A molecules and 400,000 B molecules were randomly distributed within this cell.
FIG. 8B illustrates an exemplary embodiment, showing that positions of A, B, C molecules were NOT convolved with the PSF. Instead, a super resolution microscope was assumed to create the FISH experiments undoing the effect of PSF blurring for first hyb. First hyb and second hyb had only common 20,000 A molecules, but 400,000 B and C molecules were uncorrelated.
FIG. 8C illustrates an exemplary embodiment, showing that positions of A, B, C molecules were NOT convolved with the PSF. Instead, a super resolution microscope was assumed to create the FISH experiments undoing the effect of PSF blurring for second hyb. First hyb and second hyb had only common 20,000 A molecules, but 400,000 B and C molecules were uncorrelated.
FIG. 8D illustrates an exemplary embodiment, showing cross-correlation of first and second hyb images provided this correlation function with a Gaussian in the center of the correlation result.
FIG. 8E illustrates an exemplary embodiment, showing that the background was averaged.
FIG. 8F illustrates an exemplary embodiment, showing that the cross-section of the Gaussian in the correlation image was plotted to subtract the peak value from background.
FIG. 8G illustrates an exemplary embodiment, showing that the common number of A molecules was 20,000 (expected: bar 1) and correlation function provided shared molecules in between hybs as around 18,000 (calculated: bar 2). Two bars agreed decently with 10% error.

Similar to FIGS. 7A through 7I, FIG. 8A through 8H included 20,000 A molecules but much higher 400,000 B and 400,000 C molecules in first and second hyb images. FIG. 8G presents the detection of 20,000 expected A molecules in the presence of other uncorrelated each 400,000 B and C molecules in hybs 1 and 2 respectively. Bar plot revealed about 18,000 A molecules from correlation calculation while the expected number of A molecules was around 20,000. This shows about 10% error in the calculations. Considering the density of these objects, this is fairly good estimate for single cell applications.

In comparison to the wide field PSF based images, super resolved images achieved detection of larger number of molecules in FISH images.

Example 5

Additional Results from Simulations

Figure 9:
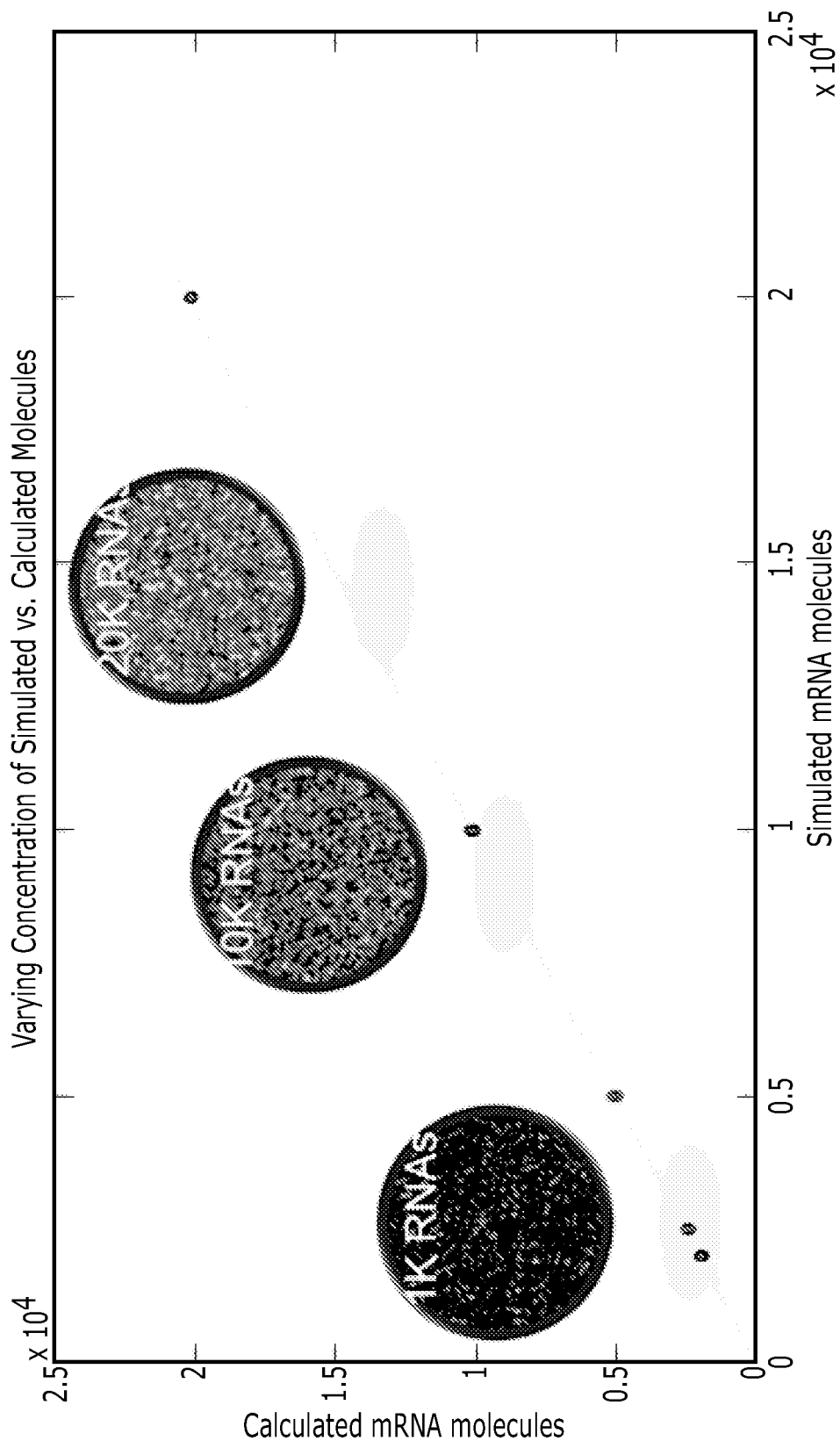
FIG. 9 illustrates an exemplary embodiment, showing auto-correlation based processing of RNA molecule images accurately predicted the number of simulated molecules in the range of 0-25,000. n=5 different runs have been processed for each data point.

The increasing concentration of the molecules was compared to the detected number of molecules within the range of 0-25,000 molecules. The auto-correlation result agreed well with the number of expected molecules creating a linear curve of detection (FIG. 9). Several data points from this curve covering 1,000, 10,000, and 20,000 molecules are depicted in the insets. n=5 different runs have been processed for each data point.

The effect of non-colocalizing molecules on the detection of co-localizing molecules was evaluated using 3 different RNA images (RNA 1-2- and 3). RNA 1 or Molecule 1 was kept constant as the numbers of other molecules were increased by up to 10 folds. The constant values of RNA1 were 10,000 or 20,000 or 30,000 or 40,000 or 50,000 or 60,000 or 70,000 molecules. For each value of RNA1, the numbers of RNA2 and RNA 3 were increased from 10,000 to 80,000. The detected values of RNA1 did not deviate from the line towards the increasing line direction in FIGS. 10A through 10C. n=3 different runs have been processed for each data point.

Example 6

Experimental Data

Figure 11B:
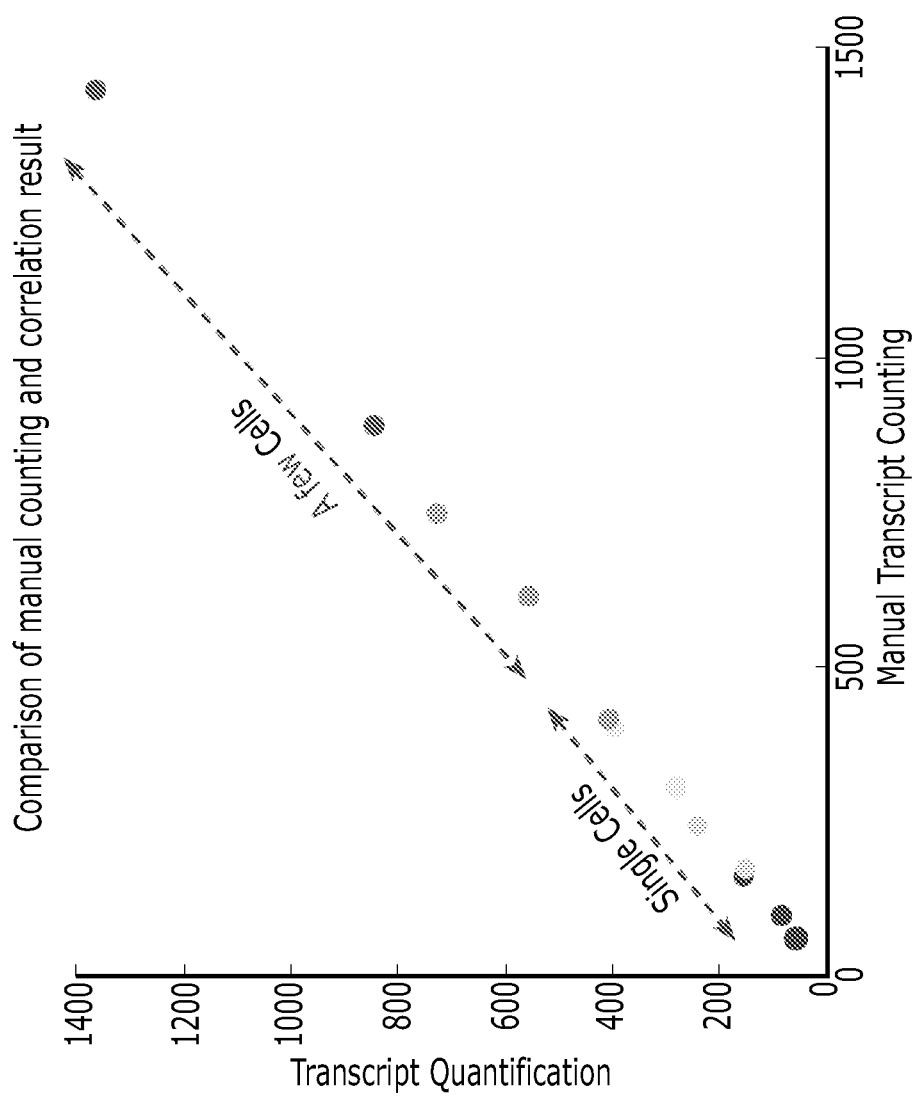
FIG. 11B illustrates exemplary embodiment, showing that manual transcript counting (based on localization of individual RNAs) and autocorrelation based transcript counting of RNAs agreed well with each other verifying the applicability of the method to the experimental settings.
Figure 11A:
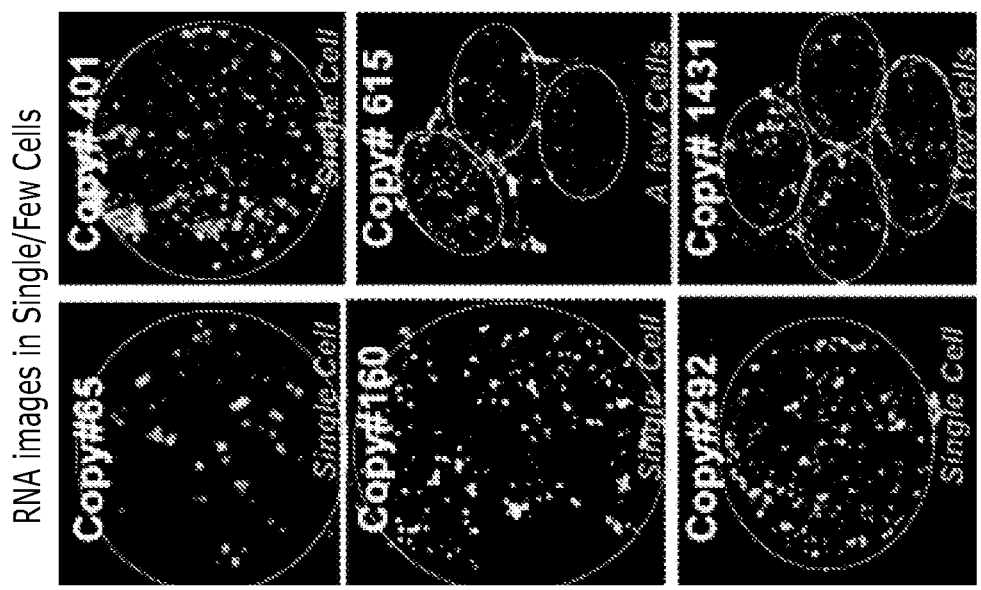
FIG. 11A illustrates exemplary embodiment, showing image correlation based quantification of RNA molecules in cells. FISH method was used to label RNA molecules. The target RNA was for Actβ housekeeping gene. Here, a single or few cell images of Actβ RNAs with copy number range of 60-500 per cell.

The presented correlation based molecule abundance quantitation method was evaluated in the FISH images of mammalian cells. First, success rate of the autocorrelation based counting was validated in cells. The target molecule was RNA for Beta Actin (Actβ) housekeeping gene exhibiting high expression in the individual cells. The abundance varied between 60-500 copies per single cells (FIG. 11A). Using single or few cells, the transcript molecule quantitation was quantified by image correlation method and compared against localization based counting (FIG. 11B). These two different calculation methods (correlation vs. localization) were plotted against each other, providing a linear curve with high regression values (R>0.9).

Figure 12A:
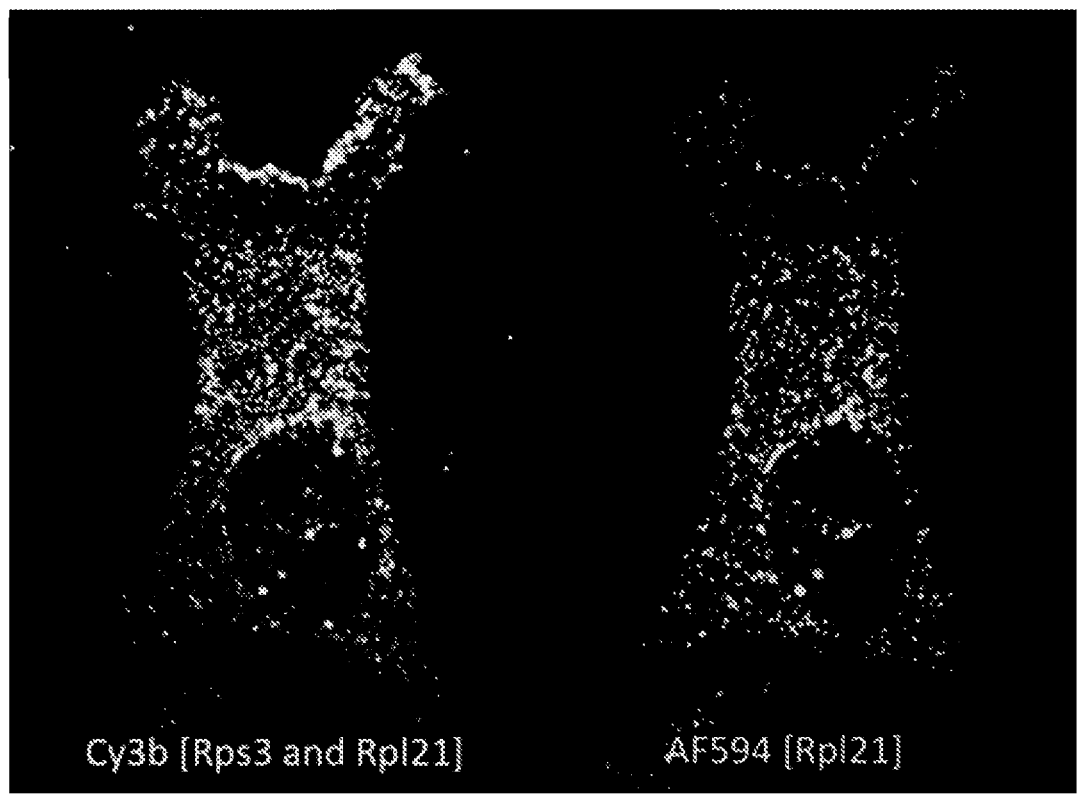
FIG. 12A illustrates exemplary embodiment, showing that RNA molecules for ribosomal protein genes were labeled with FISH probes in two subsequent hybridizations to evaluate the accuracy of cross-correlation based molecule quantitation. Here, FISH images in Cy3b and Alexa Fluor 594 color channels were presented. Rpl21 was labeled with dual color probes appearing in both channels, while Rps3 was just labeled with Alexa 594 dye.
Figure 12B:
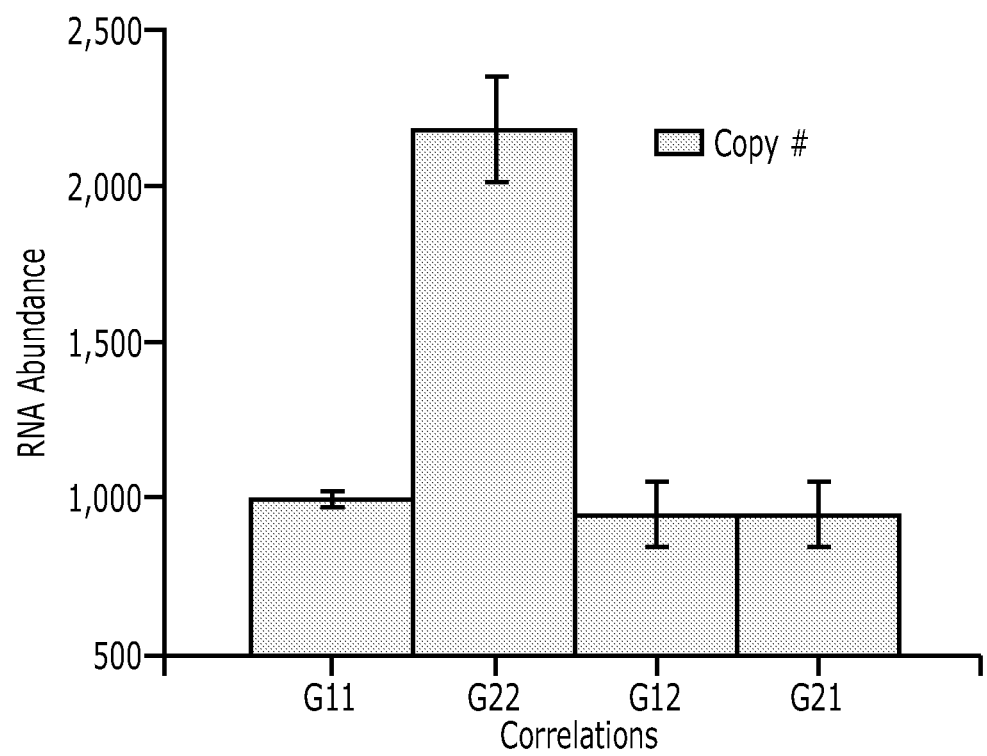
FIG. 12B illustrates exemplary embodiment, showing that the autocorrelation (G11) of the AF594 image provided around 1,000 molecules and the autocorrelation of Cy3b (G22) detected about 2,500 molecules. The cross-correlation (G12 and G21) of these two color channels enabled detection of shared gene in between Cy3b and AF594 channels providing the copy number of Rpl21 in the order of 1,000 molecules. The results from G11 and G12 agree well with each other verifying the detection accuracy of the presented image correlation quantification method.

Next, cross-correlation based abundance quantitation was evaluated in mammalian cells. FISH images of ribosomal protein genes were obtained in fibroblast cells. RNA molecules for Rps3 and Rpl21 genes were labeled with Cy3b dye and RNA for Rpl21 was dual labeled with another dye Alexa 594. RNA images of both genes were obtained from the Cy3b channel while only RNA image of Rpl21 was captured in the Alexa 594 channel of the microscopic images (FIG. 12A). Cross-correlating these two image channels provided the number of RNA molecules that are common in both images. In this case, Rpl21 was shared gene in both channels, and thus, the cross-correlation result revealed the copy number of Rpl21, that is around 1,000 RNA molecules (FIG. 12B).

Autocorrelation based quantification of both channels provided the number of total molecules in both channels, covering 1,000 average molecules and 2,350 average molecules in Alexa Fluor 594 channel and Cy3b channel, respectively (FIG. 12B). n=5 cells with similar copy numbers were used to evaluate these numbers. The total number of molecules in Alexa Fluor 594 channel should then match the cross-correlation result of the two channels. As a matter of fact, they both fall into the range of 1,000 molecules per cell validating the image correlation based molecule counting method.

Example 7

Exemplary Material and Methods

Sample Preparation

Fibroblast cells were cultured in DMEM+Glutamax+ PenStrep media and passaged every few days. Cells were plated on 24×50 mm fibronectin coated slides overnight within culture media in a petri dish. After 15 hours, glass slides were washed with PBS 1X and then fixed with 4% formaldehyde for 4 minutes. Cell were then placed in 70% ethanol for permeabilization and stored at −20° C. For experiments, glass slides with cells were dried with air blow. A custom flow-cell chamber (3 mm×11 mm Black Silicone with 0.5 mm thickness, Grace BioLabs) was then bound to this glass slide for sequential labeling of cells.

Probe Preparation 24 probes were used for each gene. Alexa 532, 594, Cy5 and Cy7 were coupled to the probes according to the ribosomal protein gene probes.

Hybridization

Fibroblasts within flow chambers were hybridized at a concentration of 1 nM per probe overnight in a hybridization buffer of 10% Dextran Sulfate (Sigma D8906), 30% Formamide, 2×SSC at room temperature. Labeled cells were then washed with 30% Formamide for 30 minutes. Samples were rinsed several times with 2×SSC to remove diffusing probes.

Microscopy

Figure 13:
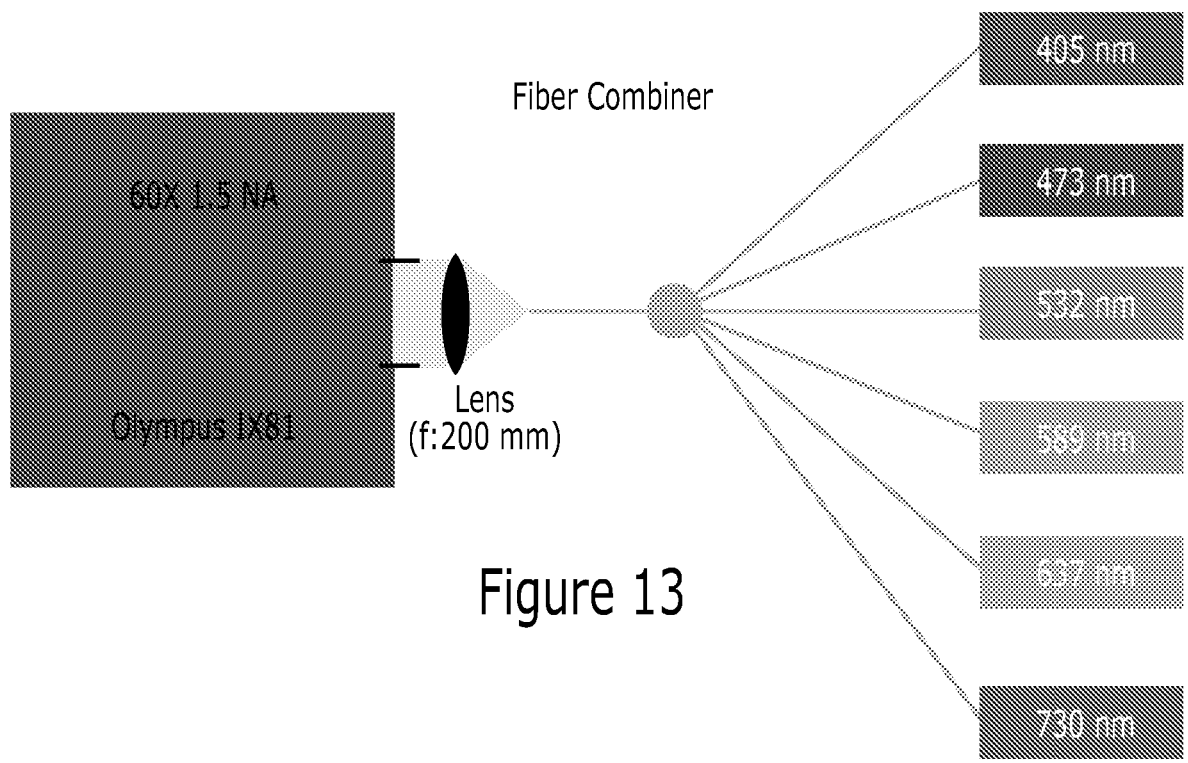
FIG. 13 illustrates an exemplary embodiment, showing a simplified wide field fluorescence microscope for single molecule imaging experiments. This approach alleviated the need for optical alignment in experimental set up for multi-color illumination of single cells. Instead, a simple fiber combiner was used to collect the light from each laser. The combined output was then collimated to the input of an Olympus IX81 microscope base for imaging experiments. A 60×1.5 NA objective lens (with 1.5× tube lens magnification) and Andor Ikon-M camera were also used to enable single molecule sensitivity for FISH experiments.

A custom fiber based single molecule imaging system was developed to enable wide field fluorescence microscopy (FIG. 13). This design removed the free space optics alignment for multi-color illumination of cells. Instead, a simple fiber combiner is used to merge to output of lasers. Each laser had about 1 Watt with 405, 473, 533, 589, 640, and 730 nm center wavelengths. 60× objective (1.4 NA) lens was used to collect single molecule FISH images. We obtained 90× magnification with the use of 1.5× tube lens magnification providing 0.144 um pixel size.

Imaging

Samples were kept in an anti-bleaching buffer consisting of 20 mM Tris-HCL, 50 mM NaCL, 0.8% Glucose, Saturated Trolox (Sigma: 53188-07-1), Pyranose oxidase (Sigma P4234) at an $OD_{405nm}$ of 0.05, and catalase at a dilution of 1/1000 (Sigma: 9001-05-2).

Data Analysis

Sequential FISH images were processed in MATLAB using a digital image-processing pipeline. Raw single molecule images were segmented to create a mask to cover the entire cell. Cell autofluorescence background was removed using the Gaussian filtered version of the same cell image to clean up correlations. This binary mask was then multiplied by the background subtracted cell images from sequential hybridizations to define the cell areas and discard other noisy patterns in the raw images. Large and bright debris on the cell surfaces were removed over a 20×20 pixels area. The pixels in the empty area were filled with the mean value of the cell. These single-cell images were then processed based on the correlation analyses yielding transcript abundances. Cells do not require spatial registration before correlation operations, making corrFISH an easy to use technique. The single-cell RNA values were then plotted as a heat map of gene expression.

Figure 14:
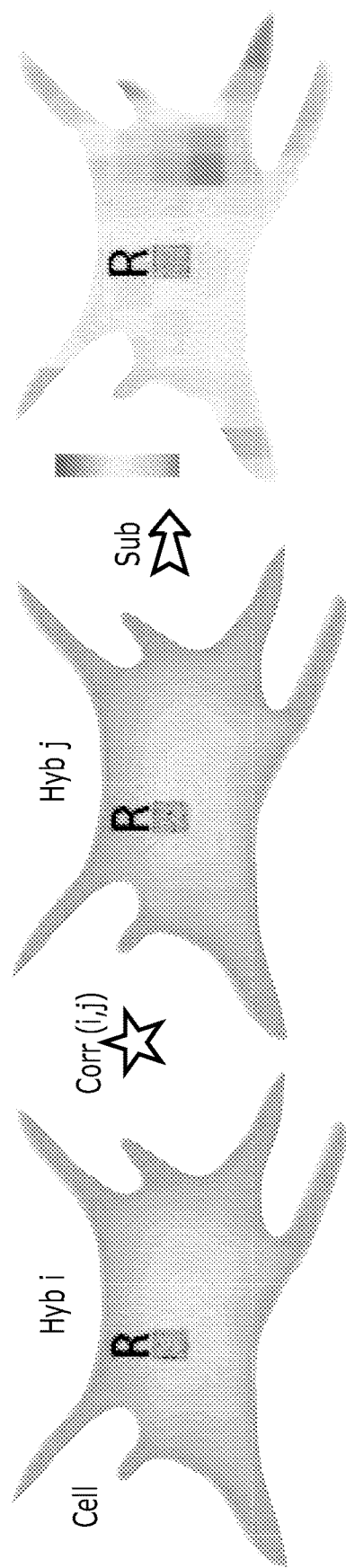
FIG. 14 illustrates an exemplary embodiment, showing that subcellular transcript quantification was performed on the subregions (R) from subsequent hybridizations. The R requires the two images to be registered. The size of R can be varied from 16 pixels to hundreds of pixels. Image can be divided into N×N blocks. Each area is assigned to a color-map for transcript abundance.

If desired, subregions of a cell can also be correlated to resolve subcellular transcript levels. For this approach, cells from two hybs were registered to define the region R (FIG. 14). Each small R was then correlated with the same area in hyb2. By repeating this process for each region in an N by N image, single cell transcripts are mapped out across the cell body.

Methods for Simulations

Point emitters were randomly distributed in a digital image of size 230×230 pixels (corresponding to 30 μm cell area) using a custom written MATLAB algorithm. Emitters were convolved with 0.4 μm width point-spread function (PSF) of a 100× wide field fluorescence microscope (0.13 μm pixel size). The obtained images mimic the molecules labeled with fluorescent dyes. Adjusting the total number of emitters per simulation area changed concentration of the molecules. Sequences of these digital images were correlated in spatial or Fourier domains to compute the abundances of molecules that are common across these image arrays. In the correlation process, PSF of the image detection does not need to be evaluated, as the correlation amplitude is the key to obtain molecule copy number.

Example 8

Simulated FISH Image Analysis

FIG. 15A-15D demonstrates a simulated analysis based on the disclosed methods using FISH images.

Figures 15A, 15B, 15C, 15D:
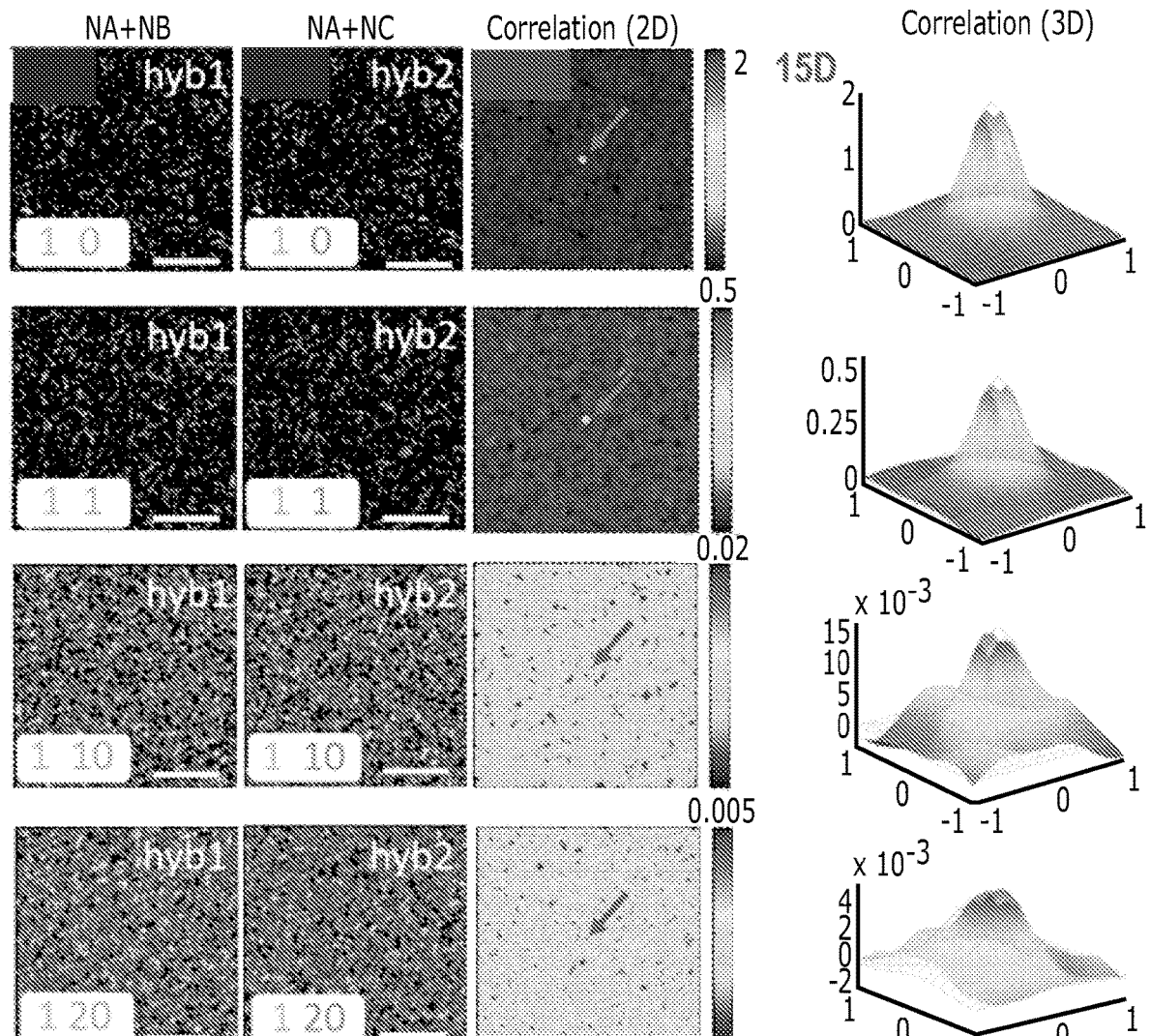
FIG. 15A illustrates an exemplary embodiment, showing simulated FISH images in 33 μm area and their correlation. Here, Hyb1 images include transcripts A and B. Density of RNA A was fixed at 1 molecule while B was changed up to 20 molecule per $\mu m^{-2}$.
FIG. 15B illustrates an exemplary embodiment, showing simulated FISH images in 33 μm area and their correlation. Here, Hyb1 images cover same A transcripts but different sets of C transcripts compared to hyb1 ones.
FIG. 15C illustrates an exemplary embodiment, showing simulated FISH images in 33 μm area and their correlation. Here, the correlation of hyb1 and hyb2 images provides a correlation matrix with a peak value in the center of the image (denoted by red arrow). Rest of the image is the background corresponding to the noise in the correlation function. Correlation noise scales up with the square root of the number of uncorrelated species. The detection of transcripts is limited by the noise competing with the peak value of the correlations.
FIG. 15D illustrates an exemplary embodiment, showing simulated FISH images in 33 μm area and their correlation. Here, a Gaussian function was then fit on to the 2×2 μm central region of the 2D correlation matrix. Gaussian fit results are presented in 3D with raw image in color and overlaid with gray best fit lines.

Simulated FISH images in 33 μm area were generated to analyze their correlations. FIG. 15A shows Hyb1 images including transcripts A and B. Density of RNA A was fixed at 1 molecule while B was changed up to 20 molecule μm-2.

FIG. 15B shows Hyb2 images covering same A transcripts but different sets of C transcripts compared to hyb 1 ones.

FIG. 15C shows the correlation of hyb1 and hyb2 images provides a correlation matrix with a peak value in the center of the image (denoted by red arrow). The rest of the image is the background corresponding to the noise in the correlation function. Correlation noise scales up with the square root of the number of uncorrelated species. The detection of transcripts is limited by the noise competing with the peak value of the correlations.

FIG. 15D shows a Gaussian function was then fit on to the 2 μm×2 central region of the 2D correlation matrix. Gaussian fit results are presented in 3D with raw image in color and overlaid with gray best fit lines.

Example 9

Dense Transcript Profiling in Single Cells by Image Correlation Decoding

Figure 16A:
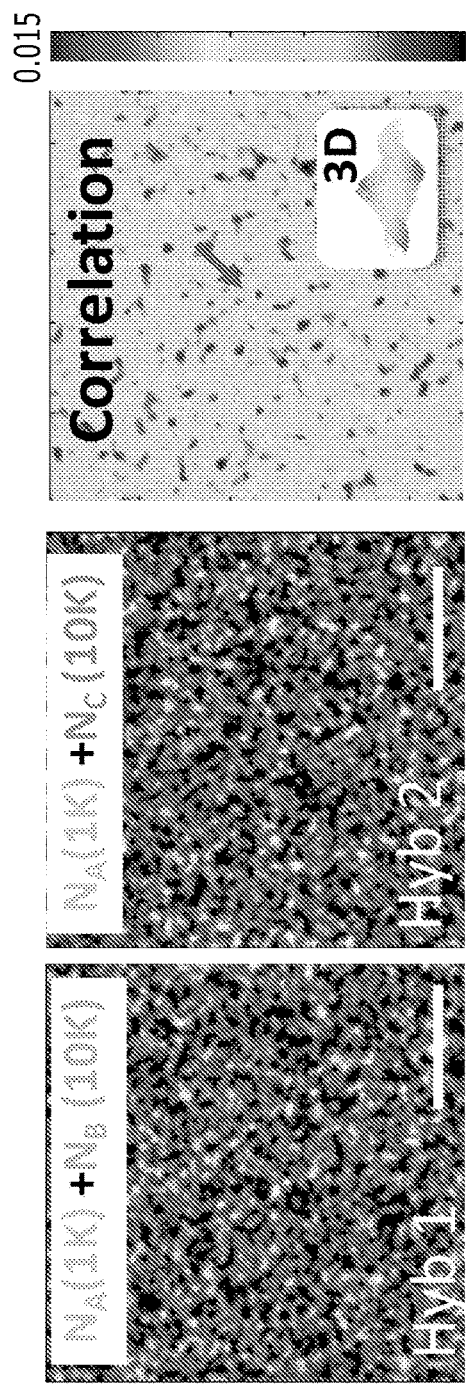
FIG. 16A illustrates an exemplary embodiment, showing simulated images of a 30 μm cell with 1000 molecule A in the presence of 10,000 molecule B or molecule C in hybridizations 1 and 2. Correlation of these images provided a peak value (denoted by the red arrow) in the middle of the resultant image. Inset showing a Gaussian function fit onto this center region. RNA density is calculated from the correlation amplitude corresponding to the copy number of A.

Recent work in sequential fluorescent in-situ hybridization (seqFISH) has demonstrated the ability to uniquely encode a large number of molecular species in single cells. However, the multiplexing capacity is practically limited by the density of the barcoded objects in the cell. Here, a general method was presented using image correlation to resolve the temporal barcodes in sequential hybridization samples, allowing high density objects to be decoded from seqFISH experiments. Using this approach, termed as correlation FISH (corrFISH), the gene expression of ribosomal proteins was profiled in single cells in cultures. Sub-cellular resolution was also demonstrated based on subregion analyses. The combination of seqFISH and correlation analyses provides a general strategy for multiplexing a large number of RNA molecules and potential to multiplexing proteins in single cells.

corrFISH does not require individual mRNA to be resolved in the image, enabling barcoding of highly abundant mRNAs. To simulate the conditions of a seqFISH experiment, we performed simulations of two rounds of hybridization with only RNA A in common between the two images with 10 fold excess of uncorrelated RNAs. RNAs are represented by a fluorescent spot with a 250 nm Gaussian point spread function distributed randomly in an area of 30 um×30 um (FIG. 16A). The cross-correlation can accurately quantify the RNA A copy number even when the spots overlap and no discernable colocalization occurs between the images. The height of the correlation peak corresponds to the copy number of A ($N_A$) as the variance of the Poisson distribution is equal to its mean. In our previous measurements, we observed that mRNA distributions in cells follow a Poisson distribution spatially. Thus the peak value at the normalized cross-correlation is a good estimator for the copy number of the A. The higher order cumulants of the Poisson distribution are all identical to the mean. Thus, the higher order cross-correlation peaks are good estimators for the abundance of the corresponding barcoded molecular species.

For simplicity, pair-wise correlation was only implemented for the proof-of-principle demonstrations. Equation 9 was used to compute correlation functions. To make the correlation faster, Fourier transform based processing is preferred in corrFISH.

$$G_{12} = \frac{\mathcal{F}^{-1}\{\mathcal{F}(H_1)\mathcal{F}(H_2)\}}{\langle H_1 \rangle \langle H_2 \rangle} \qquad \text{(Eqn. 9)}$$

where $G_{12}$ is the cross-correlation of the images from Hyb1 and Hyb2. $\mathcal{F}^{-1}$ is the inverse Fourier Transform and $\mathcal{F}$ is for the Fourier Transform operations. $H_1$ and H2 are the images. $\langle H_1 \rangle$ and $\langle H_2 \rangle$ are the mean value of the corresponding images. This approach can be extended to any pairs and dimensions of hybridizations.

These correlation results are then converted to the transcript abundance by using equation 10. The amplitude of cross-correlation is divided by the multiplication of the auto-correlation amplitudes of hyb pairs to quantity RNA copy number in a cell.

$$\langle N_{12} \rangle = \frac{G_{12}(0,0)}{G_{11}(0,0)G_{22}(0,0)} \qquad \text{(Eqn. 10)}$$

where $\langle N_{12} \rangle$ is the number of transcripts that are common across hybridizations 1 and 2. $G_{12}(0,0)$ is the amplitude of the cross-correlations of hyb 1 and 2 images. $G_{11}(0,0)$ and $G_{22}(0,0)$ are the auto-correlation amplitudes of hyb1 and hyb2, respectively.

Figure 16C:
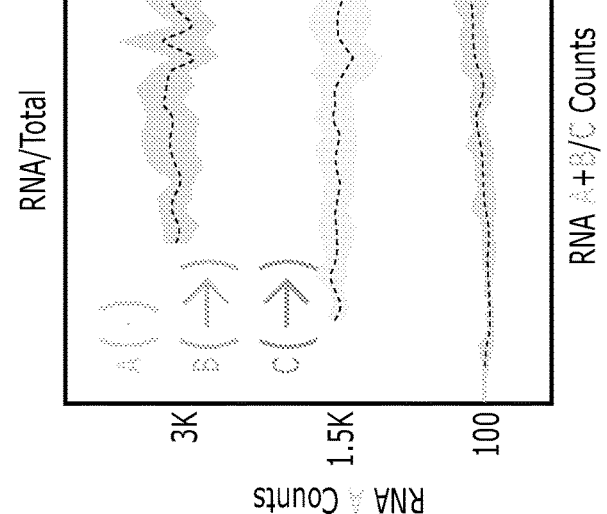
FIG. 16C illustrates an exemplary embodiment, showing quantification analysis on simulated data suggesting that even 1 molecule $\mu m^{-2}$ is detected within a total density of 100 molecule μm-2 corresponding to 1% density. RNA A density kept constant while increasing RNA B and C density.
Figure 16B:
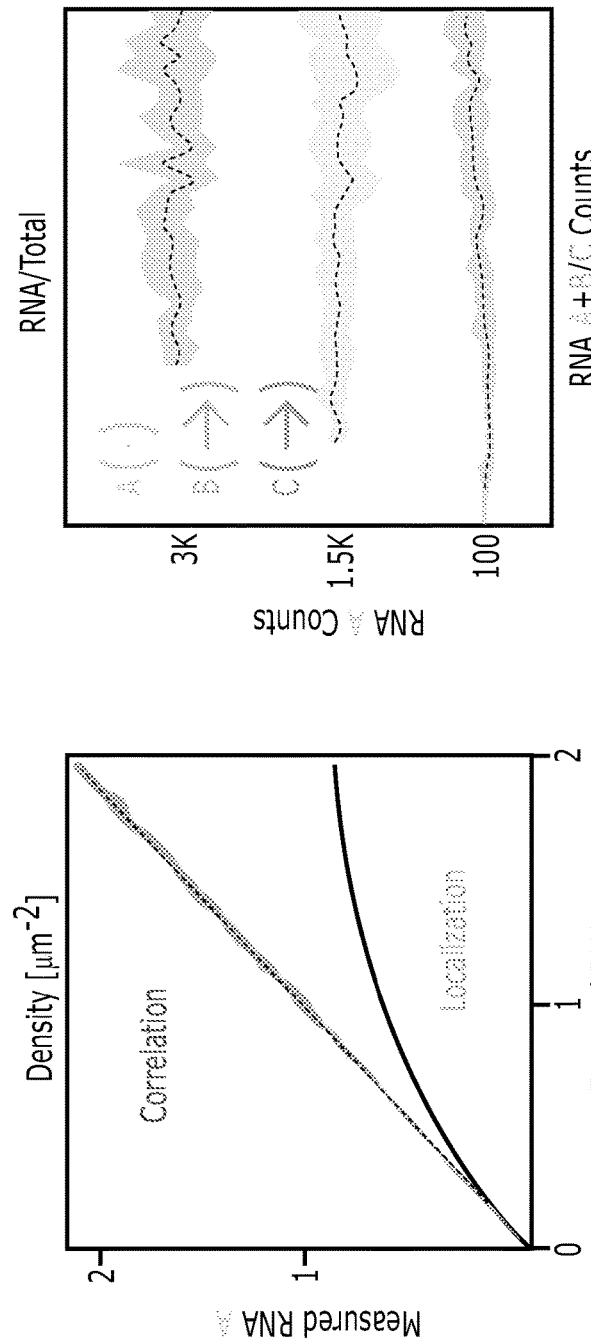
FIG. 16B illustrates an exemplary embodiment, showing that simulated RNA molecules are measured using both correlation and spatial localization for comparison. Correlation achieves higher density RNA calculations while localization starts to fail quantitation.
Figure 17A:
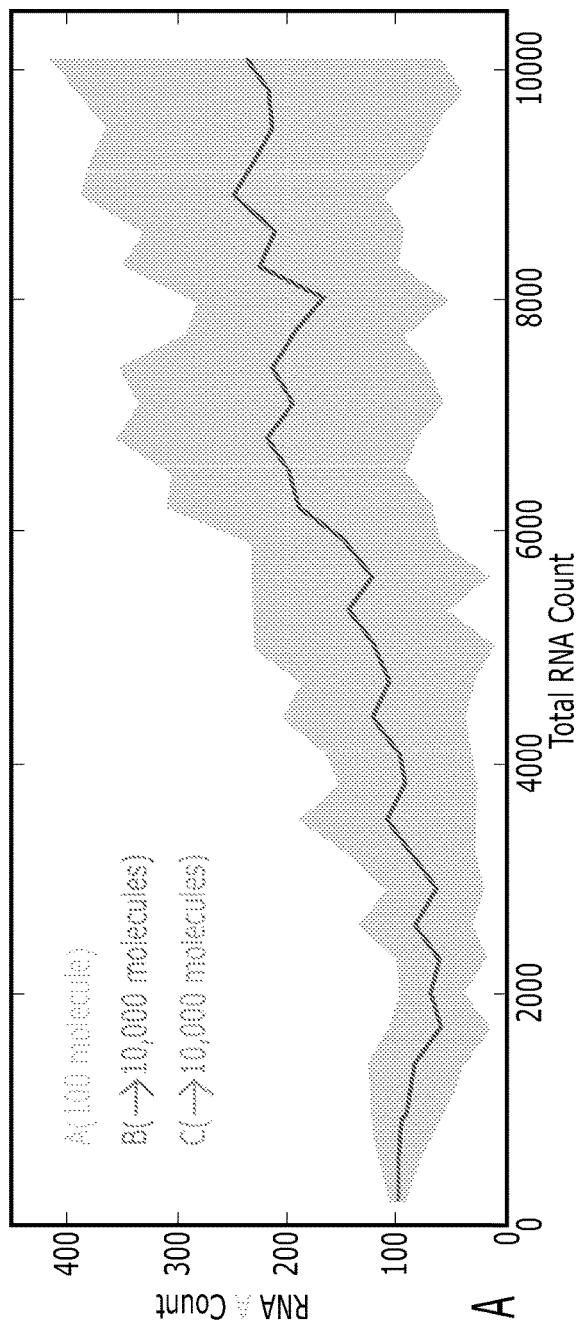
FIG. 17A illustrates an exemplary embodiment, showing transcript detection within total RNA density in 30 μm simulation cell area. RNA A was kept constant at 100 molecules while RNA B and C concentration was varied up to 10000 molecules in hyb 1 and hyb2 images, respectively. Here, the detected mean value for 100 molecules shifts up as the total transcript counts increase within the cell.
Figure 17B:
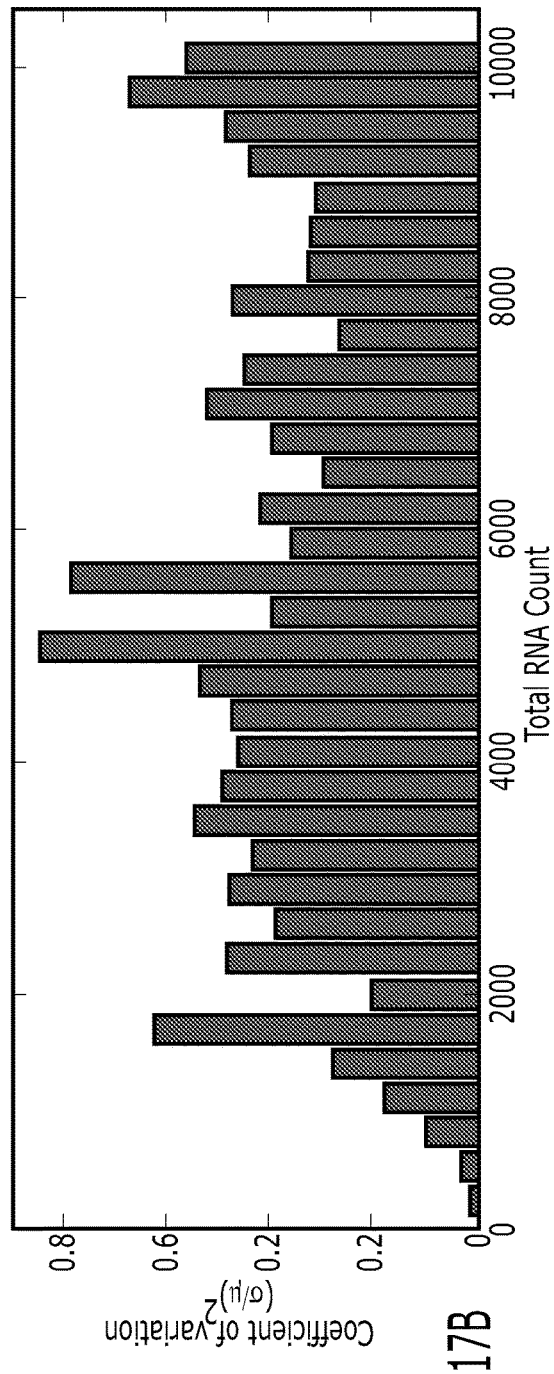
FIG. 17B illustrates an exemplary embodiment, showing the coefficient of variation (CV) analysis for detection of 100 molecules. The CV changes around 0.2-0.8 values providing good enough estimate. This sets the detection limit to be 1% in total density.

Target transcripts were measured even up to 1% of the total molecule density (FIG. 16B). For instance, 100 A molecules in 30 μm cells were accurately measured in the presence of other 10,000 B or C molecules (FIG. 16C). The coefficient of variation (CV) for detection of 100 molecules was within the range of 0.2-0.8 (FIGS. 17A and 17B). By comparison, localization based method of counting FISH spots already yield significant errors in estimating the copy number of RNAs at a density of more than 1 molecule μm$^{-2}$ (FIG. 16A and FIGS. 18A through 18F). Increasing relative amount of uncorrelated species compared to the correlated ones in images causes the localization method to fail in lower densities while only the noise is amplifying in the image correlation strategy without significant loss in transcript estimations.

Example 10

CorrFISH Analysis of Transcripts of Ribosomal Proteins

To experimentally validate this method, corrFISH was applied to measure the transcript abundances of 10 ribosomal proteins in single cells as a proof-of-principle demonstration. It has been shown that mice embryos had mosaic distribution of ribosomal protein gene expression in different tissue types. Thus it is interesting to profile the abundances of these genes at the single cell level. However, because ribosomal protein transcripts are highly abundant, it is difficult to directly measure their copy numbers using seqFISH.

Transcripts of 10 ribosomal proteins in mouse fibroblast cells were barcoded over 4 hybridizations with single color binary codes (Table 1).

Table 1. Correlation FISH barcoding scheme for 10 genes using 2 fluorophores and 4 rounds of hybridization.

| GENE | Hyb1 | Hyb2 | Hyb3 | Hyb4 | Pos Ctl | Rps2/Rps7 |
|---|---|---|---|---|---|---|
| Rpl5(Cy3b) | 0 | 0 | 1 | 1 | 0 | 0 |
| Rps6(Cy3b) | 0 | 1 | 0 | 1 | 1 | 0 |
| Rpl21(Cy3b) | 1 | 0 | 0 | 1 | 0 | 0 |
| Rps3(Cy3b) | 0 | 1 | 1 | 0 | 1 | 0 |
| Rps7(Cy3b) | 1 | 0 | 1 | 0 | 0 | 1 |
| Neg Ctl | 1 | 1 | 0 | 0 | 1 | 0 |
| Rps2(A647) | 0 | 0 | 2 | 2 | 0 | 2 |
| Rpl3(A647) | 0 | 2 | 0 | 2 | 2 | 0 |
| Rpl27a(A647) | 0 | 2 | 2 | 0 | 2 | 0 |
| Rpl23(A647) | 2 | 0 | 0 | 2 | 0 | 0 |
| Rpl18a(A647) | 2 | 0 | 2 | 0 | 0 | 0 |
| Neg Ctl | 2 | 2 | 0 | 0 | 2 | 0 |

Figure 19A:
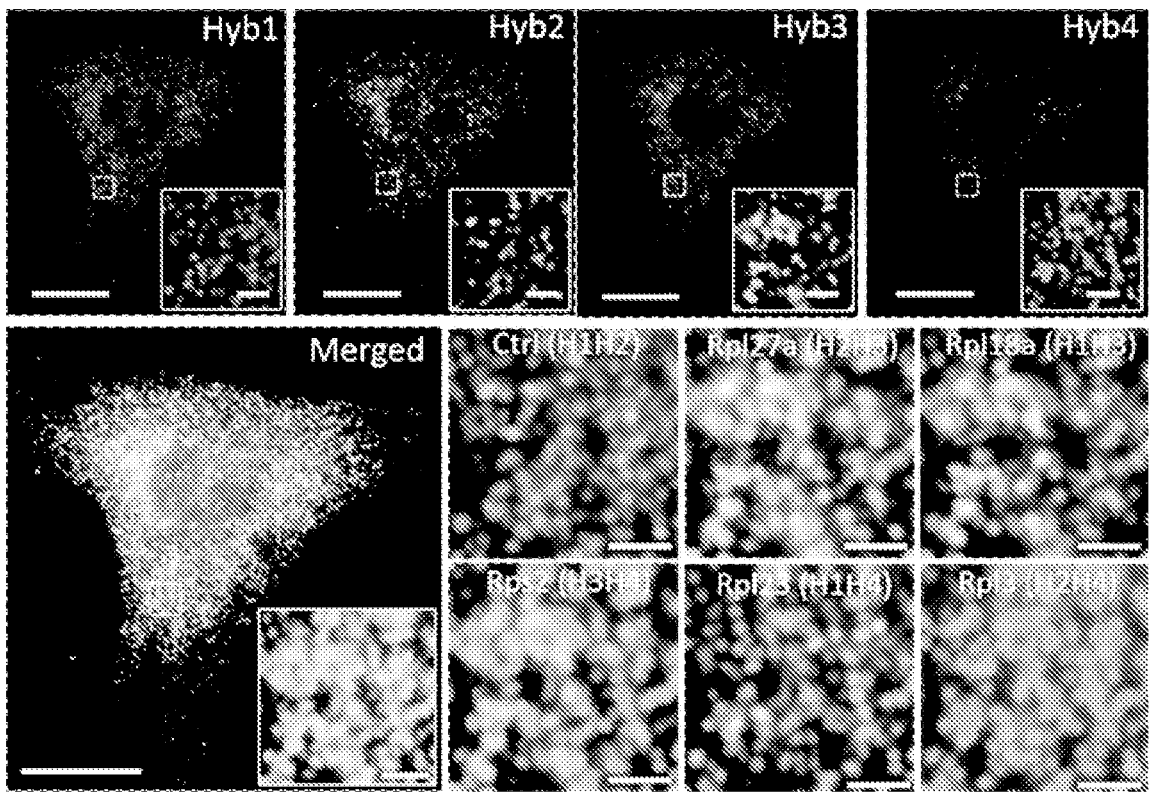
FIG. 19A illustrates an exemplary embodiment, showing that Correlation FISH in mouse fibroblasts to profile the expression of ribosomal proteins. Here, images of ribosomal protein transcripts across 4 hybridizations.
Figure 19B:
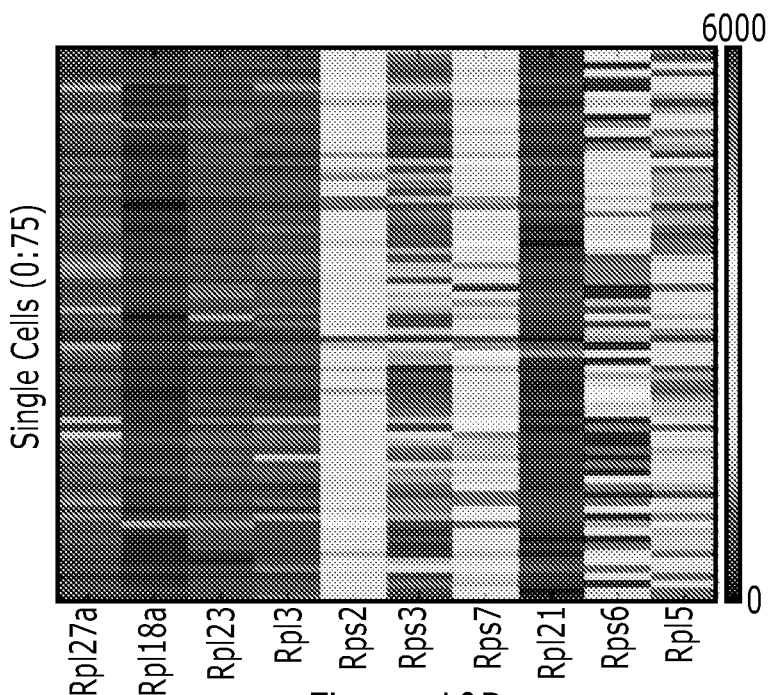
FIG. 19B illustrates an exemplary embodiment, showing a heat map for ribosomal protein transcripts in single cells (n: 75 cells) determined by the image correlations.
Figure 19C:
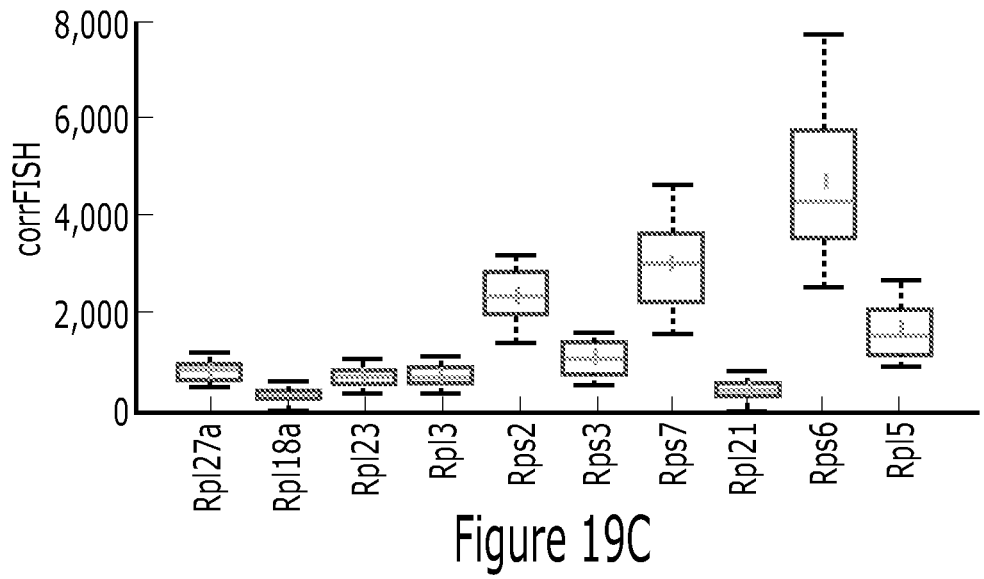
FIG. 19C illustrates an exemplary embodiment, showing Single cell RNA distributions of 10 ribosomal protein genes.
Figure 19D:
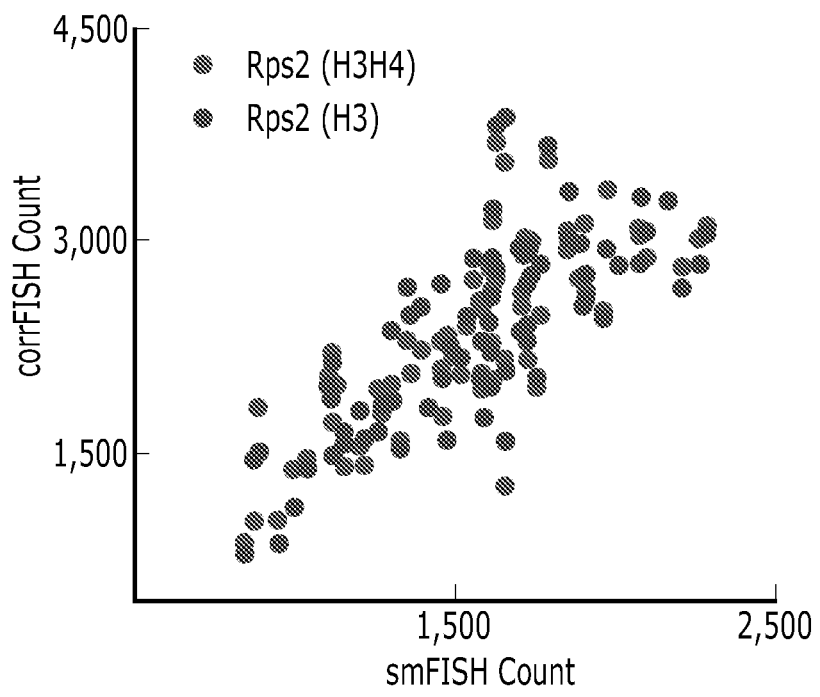
FIG. 19D illustrates an exemplary embodiment, showing Rps2 transcript quantitation by localization and correlation shows good agreement. Scale bars 20 μm and 2 (insets).
Figure 20:
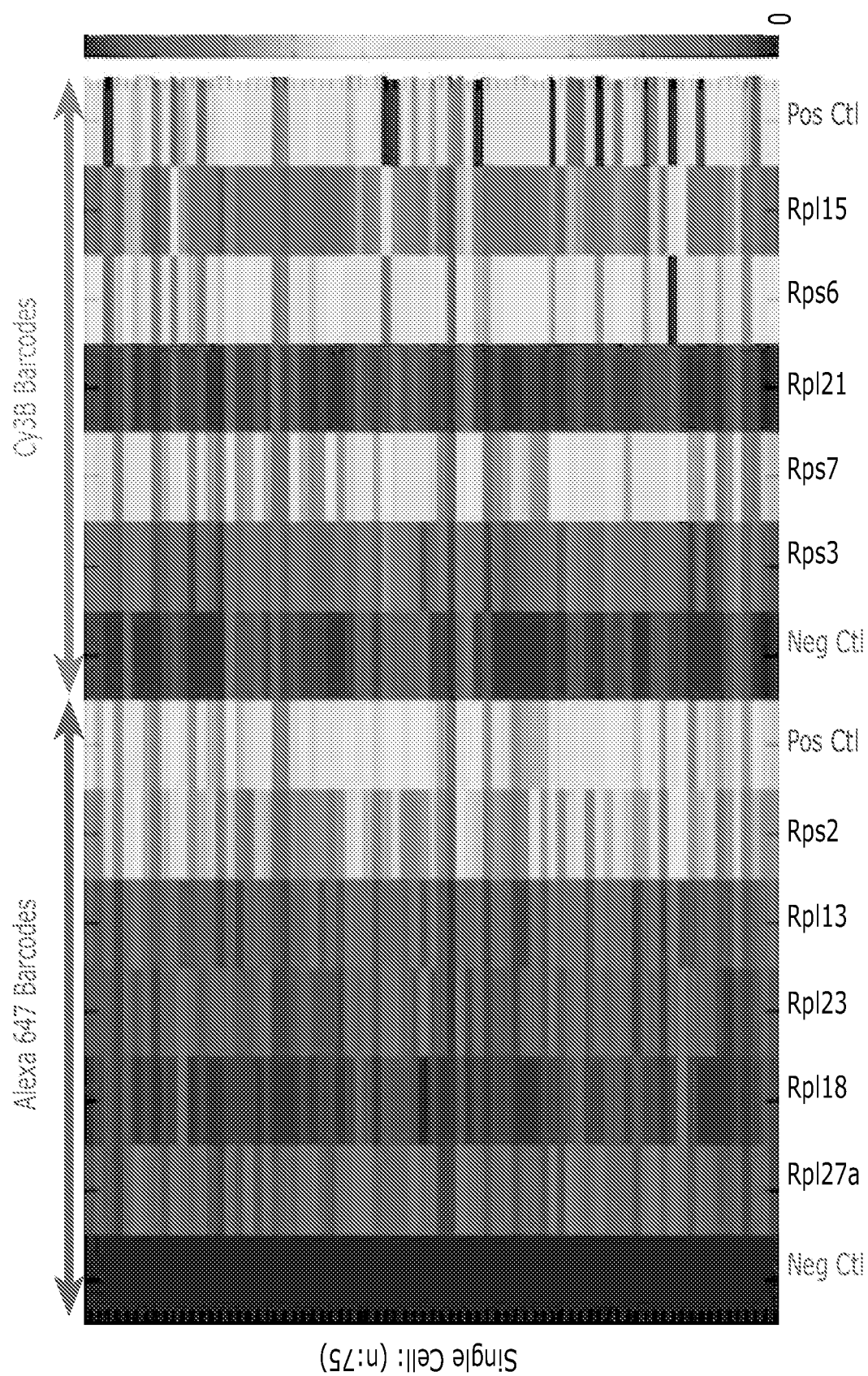
FIG. 20 illustrates an exemplary embodiment, showing that corrFISH was validated using positive and negative controls along with 10 gene detection data. No RNA is coded by H1 H2 (Neg ctrl), so no colocalization in those images are observed in this figure and no correlation is detected. Strong correlation is detected in H2 H5 (Pos Ctl), which are repeat hybridizations. Alexa 647 and Cy3B barcodes exhibited clear positive and negative signals. Cy3B had slight signal in the Neg Ctrl code due to the cellular autofluosecence background. Rps2, Rps 7, and Rps 6 genes exhibited high expression while Rpl21 and Rpl18a had low expression. corrFISH picked up these gene expression patterns agreeing well with the barcoding scheme presented in Table 1.
Figure 21A:
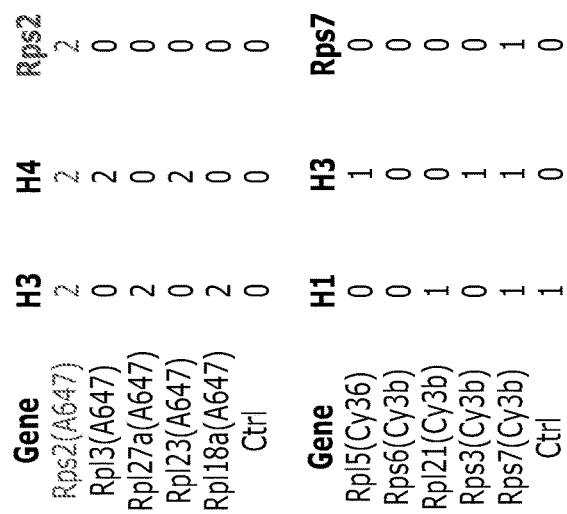
FIG. 21A illustrates an exemplary embodiment, showing that Rps2 and Rps7 genes were identified from the last hybridization to validate the corrFISH accuracy. Here, barcode assignment for Rps2 includes H3H4 correlation, H3 to the last hyb correlation, which were compared against single molecule FISH counting result. Rps7 barcodes included H1H3 correlation, H1 to the last hyb correlation, again compared to the smFISH results.
Figure 21B:
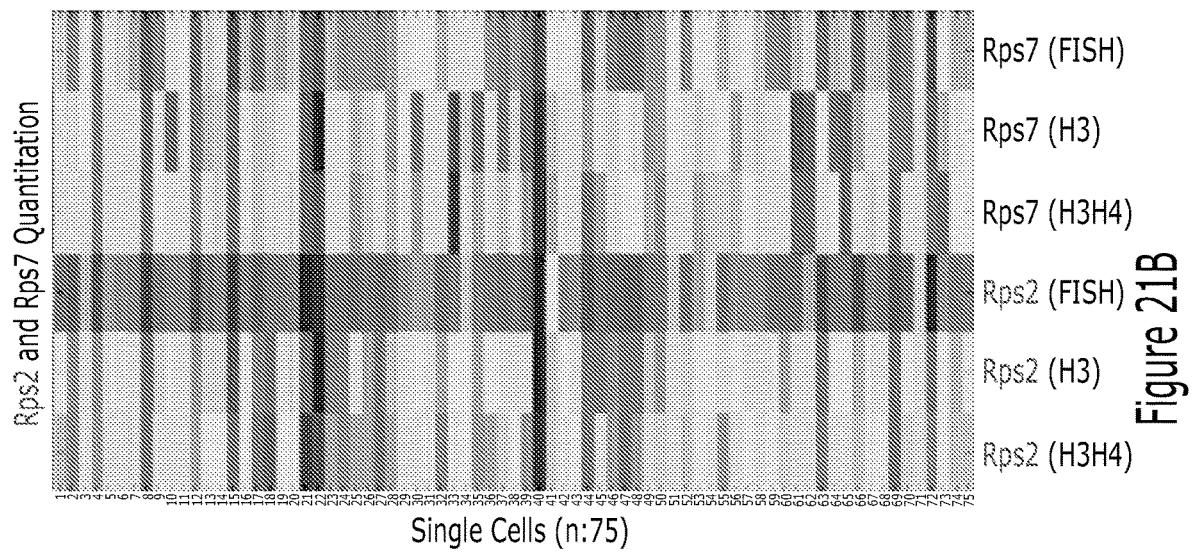
FIG. 21B illustrates an exemplary embodiment, showing that a heat map for the Rps2 and Rps7 abundance measured by these correlations and localization.
Figure 21C:
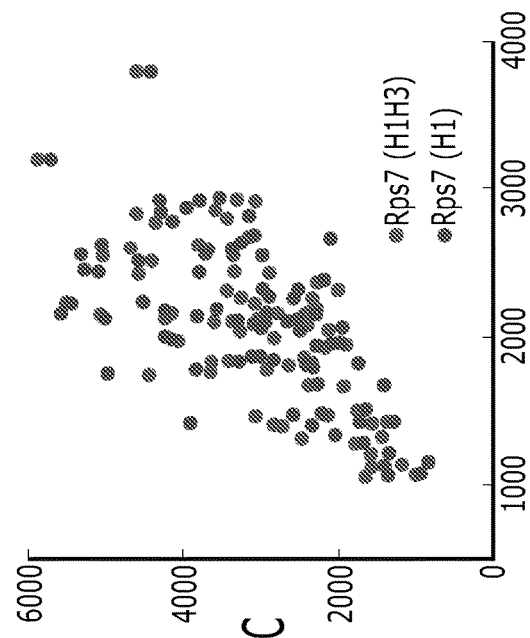
FIG. 21C illustrates an exemplary embodiment, showing that SmFISH counts Rps7 were plotted against H1 (blue) and H1H3 results (magenta) agreeing well with each other. Note that smFISH counting underestimates these counts in single cells due to the poor performance of smFISH at high densities.
Figure 22A:
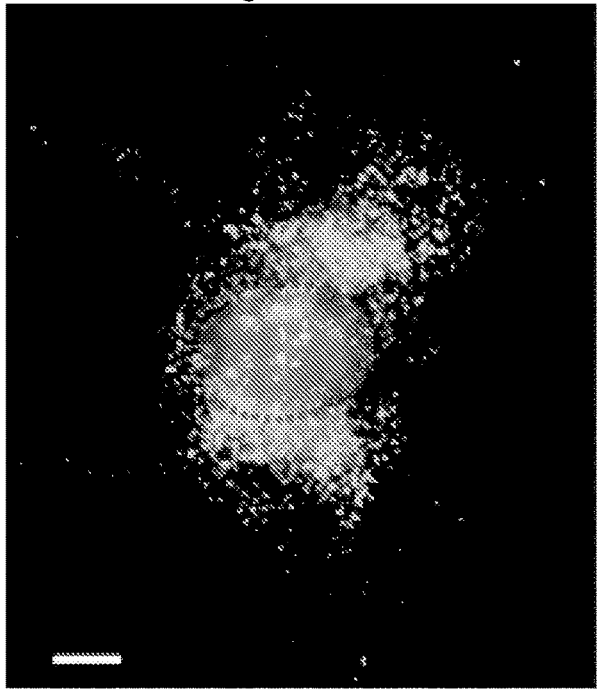
FIG. 22A illustrates an exemplary embodiment, showing subcellular analysis via corrFISH. Here, Fibroblast cell with ribosomal protein transcripts is shown in green with the nucleus in blue.
Figure 22B:
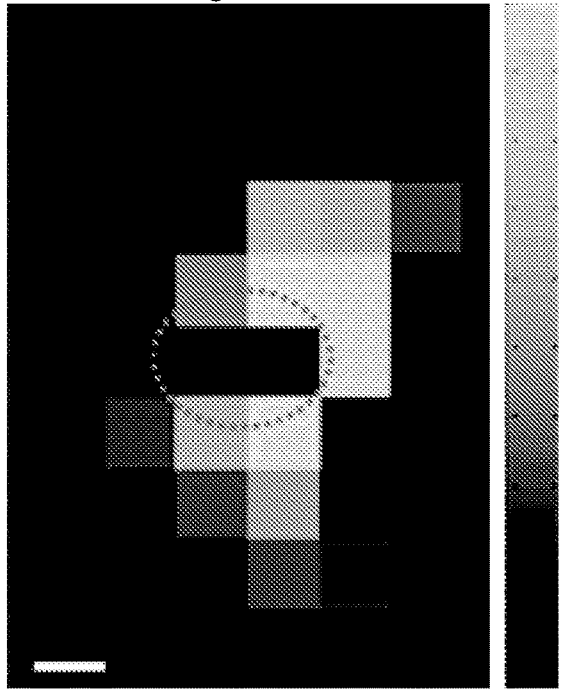
FIG. 22B illustrates an exemplary embodiment, showing correlation based transcript abundance mapping over 100 sub-regions within the cell of 22A. Dashed circle shows the nuclear region in both of the microscopic images and correlation based transcript quantification result. Scale bar 10 μm.
Figure 22C:
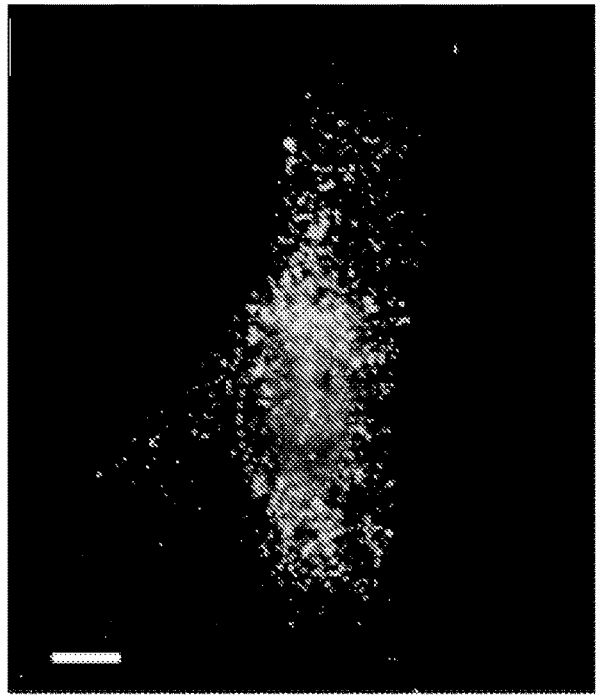
FIG. 22C illustrates an exemplary embodiment, showing another fibroblast with original image.
Figure 22D:
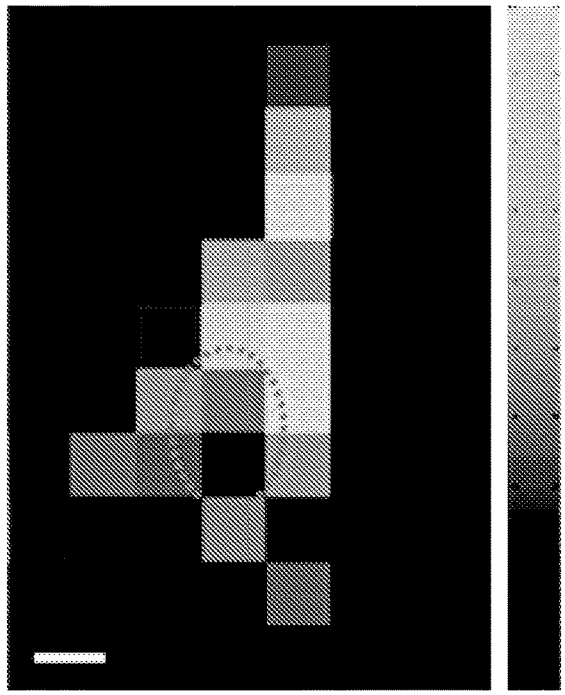
FIG. 22D illustrates an exemplary embodiment, showing transcript map corresponding to 22C. Dashed circle shows the nuclear region in both of the microscopic images and correlation based transcript quantification result. Scale bar 10 μm.

Fibroblast cells exhibited high copy number transcripts in the range of 0.5-1 molecule $\mu m^{-2}$ or 1000 copies for ribosomal proteins (FIG. 19A). Five of ribosomal protein genes (Rpl27a, Rpl18a, Rpl23, Rpl3, and Rps2) were barcoded by sequential hybridizations of Alexa 647 fluorophores, and the second set of genes (Rps3, Rps7, Rpl21, Rps6, and rpl5) was coded by Cy3B dye. Heat map of 10 genes showed significant variability in single cells (FIG. 19B). Rps6 had the highest expression level while Rpl21 and Rpl18a had the lowest (FIG. 19C). As a negative control (denoted as Ctl), empty barcodes (the correlation of hybs 1 and 2) showed negligible correlation values (FIG. 20). Two additional rounds of hybridization were performed for positive control and validation. The positive control, where the probes used for hyb 2 is used again for hyb 5 provided the highest correlation signal. For validation with smFISH, $6^{th}$ hybridization with Rps2 and Rps7 probes were performed only per color channel. Rps2 expression level determined by localization method is consistent with those quantified by cross-correlating hybs 3 to 4 (regular barcode) and hybs 3 to 6 (Rps 2 common). Rps2 was also quantified by localization of transcripts from the $6^{th}$ hyb and compared against the correlation results (FIG. 19D). These transcript values provided decent agreement ($R^2 > 0.7$) in the single molecule FISH counting (x axis) to the correlation measurement with h34 (magenta) and h36 plot (blue). Same analyses were also performed for Rps7 validating the corrFISH quantification capability (FIG. 21).

Subcellular details are also resolved by performing correlation analysis on subregions within cells (FIG. 22 and FIG. 14). Transcript distribution within a cell was mapped out in 100 subcellular regions (FIG. 22). In most of the fibroblast cells, ribosomal protein transcripts are detected outside of the the nuclear region (circled), which is detected in the sub-region correlation analysis.

The multiplex capacity of the strategy outlined here can be extended with additional rounds of hybridization and additional fluorophores. With 7 rounds of hybridization to code for 2C7=21 in each channel and 4 readily detectable fluorophores for smFISH, there are a total of 21×4=84 barcodes that can be used to cover all ribosomal protein mRNAs.

Inexpensive methods of generating FISH probes will allow us to extend this method to code for all 78 ribosomal proteins mRNAs. This implementation of corrFISH keeps the barcoding within each fluorophore channel to avoid errors introduced by chromatic aberration. The multiplexing capacity of this approach scales as $$F \times \binom{N}{k}, \quad \text{(Eqn. 11)}$$

where F is the number of fluorophore channels, N is the rounds of hybridizations, and k is the dimensionality of the correlation analysis. Incorporating chromatic corrections can further scaled up the multiplexing capacity to the exponential rate seen in the seqFISH method.

The simple demonstration of corrFISH shows that resolving single molecule FISH spots is not required to quantify RNA abundances, unconstraining the seqFISH approach to target RNAs with much higher expression levels. Conceptually, this is similar to the ability of fluorescence correlation spectroscopy (FCS) to quantify molecular concentration down to the single molecule level even in high concentration solutions. In this case, the time is generated by sequential rounds of hybridization rather than real time. This image correlation approach can be applied to decode other high density images to multiplex other molecular species other than RNA.

REFERENCES

1. Lubeck, E., Coskun, A. F., Zhiyentayev, T., Ahmad, M. & Cai, L. Single-cell in situ RNA profiling by sequential hybridization. Nat. Methods 11, 360-361 (2014).
2. Chen, K. H., Boettiger, A. N., Moffitt, J. R., Wang, S. & Zhuang, X. Spatially resolved, highly multiplexed RNA profiling in single cells. Science 348, aaa6090 (2015).
3. Lee, J. H. et al. Highly multiplexed subcellular RNA sequencing in situ. Science 343, 1360-1363 (2014).
4. Ke, R. et al. In situ sequencing for RNA analysis in preserved tissue and cells. Nat. Methods 10, 857-860 (2013).
5. Raj, A., van den Bogaard, P., Rifkin, S. A., van Oudenaarden, A. & Tyagi, S. Imaging individual mRNA molecules using multiple singly labeled probes. Nat. Methods 5, 877-879 (2008).
6. Lubeck, E. & Cai, L. Single-cell systems biology by super-resolution imaging and combinatorial labeling. Nat. Methods 9, 743-748 (2012).
7. Holden, S. J., Uphoff, S. & Kapanidis, A. N. DAOSTORM: an algorithm for high- density super-resolution microscopy. Nat. Methods 8, 279-280 (2011).
8. Zhu, L., Zhang, W., Elnatan, D. & Huang, B. Faster STORM using compressed sensing. Nat. Methods 9, 721-723 (2012).
9. Costantino, S., Comeau, J. W. D., Kolin, D. L. & Wiseman, P. W. Accuracy and Dynamic Range of Spatial Image Correlation and Cross-Correlation Spectroscopy. Biophys. J. 89, 1251-1260 (2005).
10. Xue, S. & Barna, M. Specialized ribosomes: a new frontier in gene regulation and organismal biology. Nat. Rev. Mol. Cell Biol. 13, 355-369 (2012).
11. Kondrashov, N. et al. Ribosome-mediated specificity in Hox mRNA translation and vertebrate tissue patterning. Cell 145, 383-397 (2011).
12. Magde, D., Elson, E. & Webb, W. W. Thermodynamic Fluctuations in a Reacting System-Measurement by Fluorescence Correlation Spectroscopy. Phys. Rev. Lett. 29, 705-708 (1972).
13. Swoboda, M. ACS Nano 6, 6364-69 (2012).

14. Kettling, U., Koltermann, A., Schwille, P. & Eigen, M. Proc. Natl. Acad. Sci. 95, 1416-1420 (1998).
15. Schwille, P. Cell Biochem. Biophys. 34, 383-408 (2001).
16. Heinze, K. G., Jahnz, M. & Schwille, P. Biophys. J. 86, 506-516 (2004)

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of determining an abundance level of at least two different molecular targets within a defined region in a cell, comprising:
 (a) providing a sample comprising the cell;
 (b) carrying out a plurality of $\{1, 2, \ldots N\}$ hybridizations on the sample, wherein N is equal or greater than 2, and wherein the plurality of hybridizations interacts with the at least two molecular targets, and wherein each hybridization is performed on the sample by applying a hybridization-specific plurality of probes to the cell, wherein each plurality of probes comprises at least two probes, one probe interacting with at least one of the two different molecular targets, and the other probe interacting with at least the other of the two different molecular targets;
(c) imaging the sample after each hybridization and obtaining an image produced by the interaction between the at least two probes of that hybridization and the at least two molecular targets, wherein the image at least partially constitutes visual data for the hybridization, and wherein at least one image per fluorophore channel per hybridization is taken;
(d) identifying, in the defined region in the cell, an abundance of the at least two molecular targets by using a correlation function, wherein the correlation function spatially correlates visual data from two or more images; and
(e) determining an abundance level of the at least two molecular targets based on the correlation function.

2. The method of claim 1, wherein the visual data comprise at least two images of the defined region of the cell for each hybridization, and wherein each of the at least two images has predetermined pixel values.

3. The method of claim 1, wherein the defined region in the cell is the entire cell.

4. The method of claim 1, wherein the defined region in the cell comprises a portion of the cell.

5. The method of claim 1, wherein the at least two molecular targets are selected from the group consisting of nucleic acid molecules, DNAs, RNAs, mRNAs, proteins, lipids, carbohydrates, and combinations thereof.

6. The method of claim 1, further comprising:
removing a preceding plurality of probes from the cell in a second or subsequent hybridization.

7. The method of claim 6, further comprising:
applying a plurality of probes to the cell after the preceding plurality of probes is removed from the cell.

8. The method of claim 1, wherein the identifying step comprises:
locating, in the visual data for each second or subsequent hybridization, a visual signal within the defined region; and
identifying, in the visual data for a preceding hybridization, a second visual signal within the defined region, corresponding to the same molecular target.

9. The method of claim 1, wherein the correlation function between the visual data for a second or subsequent hybridization and the visual data for a preceding hybridization is determined in a spatial domain.

10. The method of claim 1, wherein the visual data comprise:
an image A of the defined region for the hybridization with pixel values; and
an image B of the defined region for the second hybridization with predetermined pixel values.

11. The method of claim 1, wherein the correlation function between image A and image B is:

$$C(k, l) = \sum_{m=0}^{M-1} \sum_{n=0}^{N-1} A(m, n) B(m-k, n-l), \quad (i)$$

where M and N are dimensions of images in x axis and y axis, respectively, A and B are the images, C is the correlation matrix with k and l as the spatial lag variables;

(ii) $C(i,j) = F^{-1}\{(m,n))F^*(B(m,n))\}$, where F is the Fourier transform operation, A and B are the images, and C is the correlation matrix with i and j as the spatial lag variables; or $$G(i, j) = \frac{F^{-1}\{F(A(m, n))F^*(B(m, n))\}}{\langle A(m, n)\rangle \langle B(m, n)\rangle} - 1, \quad (iii)$$

where F is the Fourier transform operation, A and B are the images, and G is the correlation matrix with i and j as the spatial lag variables, which has been normalized.

12. The method of claim 11, wherein the abundance level is $$\langle N_{12}\rangle = \frac{G_{12}(0, 0)}{G_{11}(0, 0)G_{22}(0, 0)},$$

where $G_{12}(0,0)$ is the amplitude of the cross-correlation of image A and image B, $G_{11}(0,0)$ is the autocorrelation amplitude of image A, and $G_{22}(0,0)$ is the autocorrelation amplitude of image B.

13. The method of claim 1, wherein the plurality of hybridizations {1, 2, . . . N} further comprises:
an additional hybridization during which an additional plurality of probes is applied to the cell, wherein the additional plurality of probes comprises at least two probes interacting with the same copy of the molecular target to provide a visual signal constituting the visual data for the additional hybridization, and wherein the visual signal differs from at least two preceding visual signals.

14. The method of claim 13, further comprising:
applying the additional plurality of probes to the cell after two preceding pluralities of probes are removed from the cell.

15. The method of claim 2, further comprising:
identifying a central region of each image, wherein the central region includes a correlation amplitude; and
applying background subtraction by summing all pixel values of each image, except those pixels within the central region.

16. The method of claim 2, further comprising:
applying to each image, an image filter selected from the group consisting of deconvolution, deblurring, N-D filtering of multidimensional images, 2-D Gaussian filtering of images, 3-D Gaussian filtering of 3-D images, creating predefined 2-D filter, guided filtering of images, normalized 2-D cross-correlation, 2-D adaptive noise-removal filtering, 2-D median filtering, 2-D order-statistic filtering, local standard deviation of image, local range of image, local entropy of grayscale image, general sliding-neighborhood operations, extracting objects from binary image by size, extracting objects from binary image using properties, Pad array, 2-D frequency response, 2-D FIR filter using frequency sampling, 2-D FIR filter using frequency transformation, 2-D FIR filter using 1-D window method, 2-D FIR filter using 2-D window method, 2-D convolution matrix and combinations thereof.

17. The method of claim 1, wherein the defined region has a density of the molecular targets of at least 0.5 to 10 molecules per $\mu m^2$.

18. The method of claim 1, further comprising:
assigning a color scheme to each abundance level of the molecular targets for each defined region in the plurality of defined regions and creating a color representation of distribution of the molecular targets within the cell.

\* \* \* \* \*